United States Patent
Hummel

(10) Patent No.: US 10,688,652 B2
(45) Date of Patent: Jun. 23, 2020

(54) ROBOT CLEANER, REMOTE CONTROL SYSTEM INCLUDING THE SAME, AND CONTROL METHOD THEREOF

(71) Applicant: LG ELECTRONICS INC., Seoul (KR)

(72) Inventor: Christian Hummel, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 74 days.

(21) Appl. No.: 15/549,829

(22) PCT Filed: Feb. 15, 2016

(86) PCT No.: PCT/KR2016/001489
§ 371 (c)(1),
(2) Date: Aug. 9, 2017

(87) PCT Pub. No.: WO2016/133320
PCT Pub. Date: Aug. 25, 2016

(65) Prior Publication Data
US 2018/0021942 A1    Jan. 25, 2018

(30) Foreign Application Priority Data
Feb. 16, 2015  (KR) .................. 10-2015-0023612

(51) Int. Cl.
*B01D 46/46* (2006.01)
*B25J 9/00* (2006.01)
(Continued)

(52) U.S. Cl.
CPC .............. *B25J 9/0003* (2013.01); *A47L 9/009* (2013.01); *A47L 9/0411* (2013.01);
(Continued)

(58) Field of Classification Search
CPC ..... B25J 9/0003; A47L 9/2826; A47L 9/2894; A47L 9/2873; A47L 9/2884; A47L 9/009;
(Continued)

(56) References Cited

U.S. PATENT DOCUMENTS 5,646,494 A * 7/1997 Han ................... A47L 11/4011
318/587
9,399,284 B2 * 7/2016 Kwon .................. A47L 9/2826
(Continued)

FOREIGN PATENT DOCUMENTS

JP    2013-250005      12/2013
KR    10-2003-00155139    7/2003
(Continued)

OTHER PUBLICATIONS

International Search Report and Written Opinion dated Jun. 20, 2016 issued in Application No. PCT/KR2016/001489 (with English Translation).
(Continued)

*Primary Examiner* — Dung H Bui
(74) *Attorney, Agent, or Firm* — KED & Associates LLP

(57) ABSTRACT

A robot cleaner includes an environment information detecting unit configured to obtain environment information regarding at least a portion of a cleaning area, a first communication unit configured to transmit and receive data to and from a different device positioned within the cleaning area, and a control unit configured to generate a control command regarding the different device in order to adjust the obtained environment information.

10 Claims, 12 Drawing Sheets

(51) Int. Cl.
| | |
|---|---|
| G05D 1/02 | (2020.01) |
| H04L 12/28 | (2006.01) |
| A47L 9/00 | (2006.01) |
| A47L 9/04 | (2006.01) |
| A47L 9/12 | (2006.01) |
| A47L 9/14 | (2006.01) |
| A47L 9/28 | (2006.01) |
| A47L 9/30 | (2006.01) |
| A61L 9/12 | (2006.01) |
| A61L 9/20 | (2006.01) |
| H04L 29/08 | (2006.01) |

(52) U.S. Cl.
CPC .......... *A47L 9/0477* (2013.01); *A47L 9/0488* (2013.01); *A47L 9/12* (2013.01); *A47L 9/14* (2013.01); *A47L 9/2826* (2013.01); *A47L 9/2852* (2013.01); *A47L 9/2857* (2013.01); *A47L 9/2873* (2013.01); *A47L 9/2884* (2013.01); *A47L 9/2894* (2013.01); *A47L 9/30* (2013.01); *A61L 9/12* (2013.01); *A61L 9/20* (2013.01); *G05D 1/0242* (2013.01); *G05D 1/0255* (2013.01); *G05D 1/0274* (2013.01); *H04L 12/2816* (2013.01); *A47L 2201/022* (2013.01); *A47L 2201/04* (2013.01); *A61L 2209/111* (2013.01); *G05D 2201/0203* (2013.01); *G05D 2201/0207* (2013.01); *H04L 67/12* (2013.01)

(58) Field of Classification Search
CPC .... A47L 9/0411; A47L 9/0477; A47L 9/0488; A47L 9/12; A47L 9/14; A47L 9/2857; A47L 9/2852; A47L 9/30; A47L 2201/022; A47L 2201/04; A61L 9/12; A61L 9/20; A61L 2209/111; H04L 12/2816; H04L 67/12; G05D 1/0274; G05D 1/0255; G05D 1/0242; G05D 2201/0203; G05D 2201/027
See application file for complete search history.

(56) References Cited

U.S. PATENT DOCUMENTS

| | | | | |
|---|---|---|---|---|
| 9,675,226 B2* | 6/2017 | Kim | ............ | A47L 9/2894 |
| 2004/0178767 A1* | 9/2004 | Jeon | ............ | A47L 9/009 |
| | | | | 320/114 |
| 2004/0255425 A1* | 12/2004 | Arai | ............ | A47L 5/28 |
| | | | | 15/300.1 |
| 2005/0027395 A1* | 2/2005 | Ann | ............ | G05D 1/0234 |
| | | | | 700/245 |
| 2006/0200282 A1* | 9/2006 | Lee | ............ | G05D 1/0221 |
| | | | | 701/23 |
| 2006/0235570 A1* | 10/2006 | Jung | ............ | G05D 1/0022 |
| | | | | 700/245 |
| 2007/0021867 A1* | 1/2007 | Woo | ............ | B25J 5/00 |
| | | | | 700/245 |
| 2007/0050086 A1* | 3/2007 | Lim | ............ | G05D 1/0225 |
| | | | | 700/245 |
| 2007/0250212 A1* | 10/2007 | Halloran | ............ | A47L 5/30 |
| | | | | 700/245 |
| 2008/0276407 A1* | 11/2008 | Schnittman | ............ | A47L 11/34 |
| | | | | 15/319 |
| 2010/0313910 A1* | 12/2010 | Lee | ............ | A47L 7/02 |
| | | | | 134/6 |
| 2011/0125324 A1* | 5/2011 | Baek | ............ | G05D 1/0219 |
| | | | | 700/258 |
| 2011/0264305 A1* | 10/2011 | Choe | ............ | G05D 1/0246 |
| | | | | 701/2 |
| 2012/0051595 A1* | 3/2012 | Lee | ............ | G05D 1/0246 |
| | | | | 382/103 |
| 2012/0116588 A1 | 5/2012 | Lee et al. | | |
| 2012/0259481 A1* | 10/2012 | Kim | ............ | G05D 1/0016 |
| | | | | 701/2 |
| 2012/0265370 A1* | 10/2012 | Kim | ............ | G05D 1/0016 |
| | | | | 701/2 |
| 2013/0056032 A1* | 3/2013 | Choe | ............ | A47L 9/0488 |
| | | | | 134/18 |
| 2013/0060379 A1* | 3/2013 | Choe | ............ | G06N 3/008 |
| | | | | 700/245 |
| 2013/0116825 A1* | 5/2013 | Kim | ............ | A47L 11/20 |
| | | | | 700/259 |
| 2013/0116826 A1* | 5/2013 | Kim | ............ | G05D 1/0246 |
| | | | | 700/259 |
| 2013/0218344 A1* | 8/2013 | Teng | ............ | A47L 11/4061 |
| | | | | 700/259 |
| 2013/0232717 A1* | 9/2013 | Lee | ............ | G05D 1/0255 |
| | | | | 15/319 |
| 2013/0326839 A1* | 12/2013 | Cho | ............ | A47L 9/2805 |
| | | | | 15/319 |
| 2013/0331990 A1* | 12/2013 | Jeong | ............ | G01S 17/936 |
| | | | | 700/259 |
| 2014/0095164 A1* | 4/2014 | Sone | ............ | H04L 51/16 |
| | | | | 704/260 |
| 2014/0156076 A1* | 6/2014 | Jeong | ............ | B25J 9/0003 |
| | | | | 700/257 |
| 2014/0195011 A1* | 7/2014 | Sakuta | ............ | G08C 17/00 |
| | | | | 700/11 |
| 2014/0244094 A1* | 8/2014 | Kim | ............ | G05D 1/021 |
| | | | | 701/23 |
| 2014/0303775 A1* | 10/2014 | Oh | ............ | G05D 1/0016 |
| | | | | 700/253 |
| 2014/0316636 A1* | 10/2014 | Hong | ............ | G05D 1/0016 |
| | | | | 701/27 |
| 2014/0336863 A1* | 11/2014 | So | ............ | G05D 1/0219 |
| | | | | 701/28 |
| 2015/0052703 A1* | 2/2015 | Lee | ............ | A47L 9/2815 |
| | | | | 15/319 |
| 2015/0150428 A1* | 6/2015 | Park | ............ | A47L 11/4005 |
| | | | | 134/18 |
| 2016/0000290 A1* | 1/2016 | Kwak | ............ | A47L 11/4011 |
| | | | | 700/253 |
| 2016/0039095 A1* | 2/2016 | Ho | ............ | G01S 17/936 |
| | | | | 700/253 |
| 2016/0089783 A1* | 3/2016 | Noh | ............ | G06K 9/00671 |
| | | | | 382/153 |
| 2016/0135655 A1* | 5/2016 | Ahn | ............ | A47L 9/2826 |
| | | | | 134/56 R |
| 2016/0149996 A1* | 5/2016 | Eckert | ............ | H04L 43/06 |
| | | | | 709/217 |
| 2016/0274579 A1* | 9/2016 | So | ............ | A47L 9/2852 |
| 2017/0097232 A1* | 4/2017 | Anderson-Sprecher | ............ | G05D 1/021 |
| 2017/0132568 A1* | 5/2017 | Glunz | ............ | G06T 19/00 |
| 2017/0227961 A1* | 8/2017 | Baroudi | ............ | G05D 1/0287 |
| 2017/0360266 A1* | 12/2017 | Izawa | ............ | G06T 7/579 |
| 2018/0028033 A1* | 2/2018 | Jung | ............ | A47L 9/28 |

FOREIGN PATENT DOCUMENTS

| | | |
|---|---|---|
| KR | 10-2012-0114671 | 10/2012 |
| KR | 10-2012-0116283 | 10/2012 |
| KR | 10-2014-0063119 | 5/2014 |

OTHER PUBLICATIONS

European Search Report dated Oct. 9, 2018 issued in Application No. 16752650.8.

* cited by examiner

[Fig. 1]
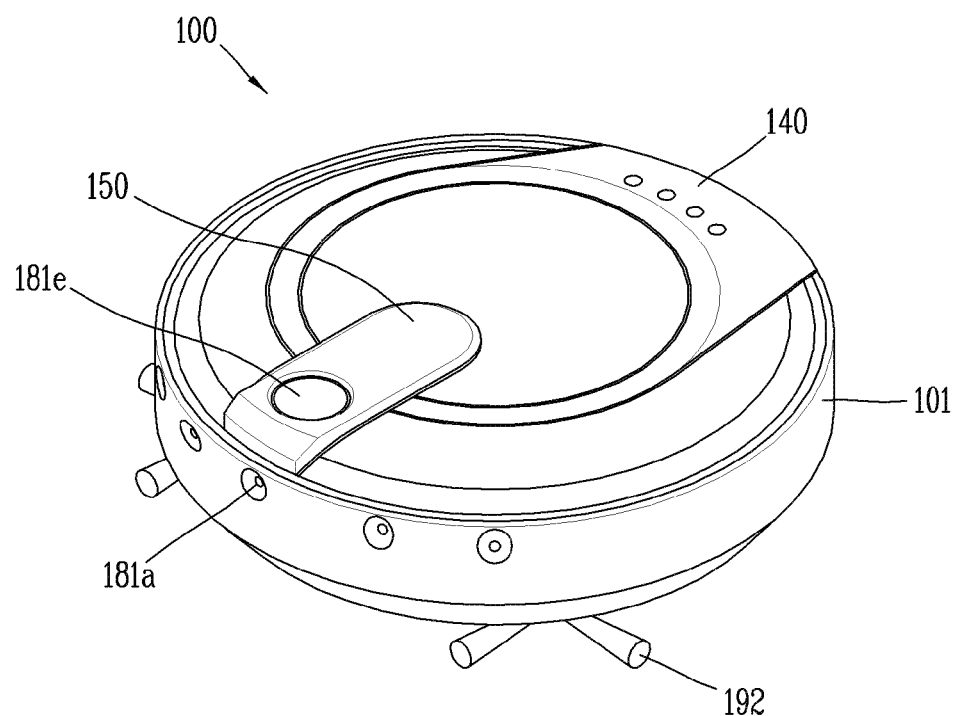
[Fig. 2]
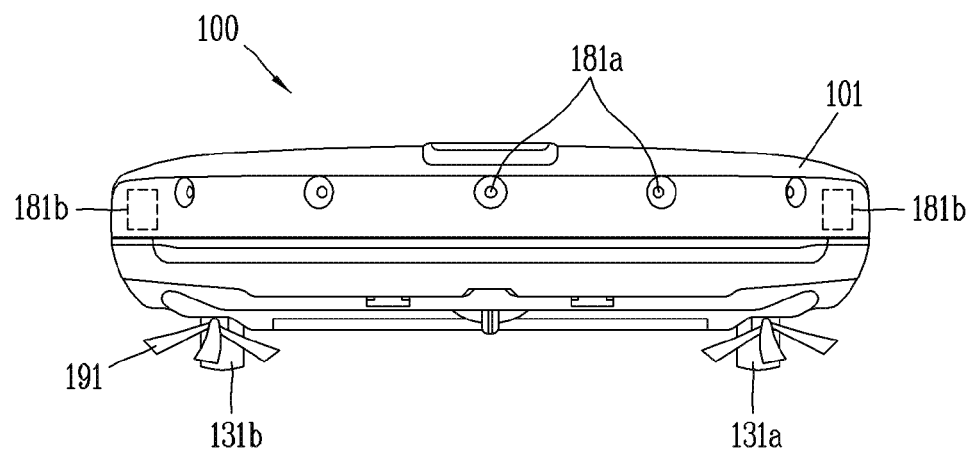

[Fig. 3]
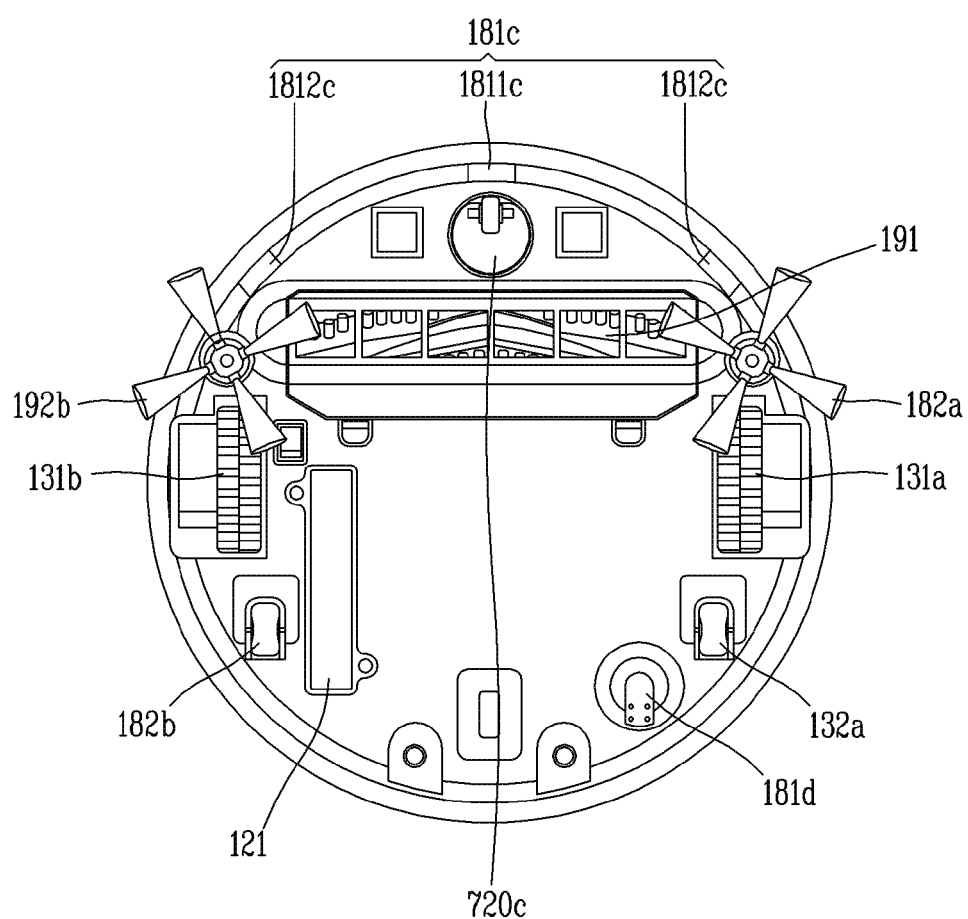

[Fig. 4]
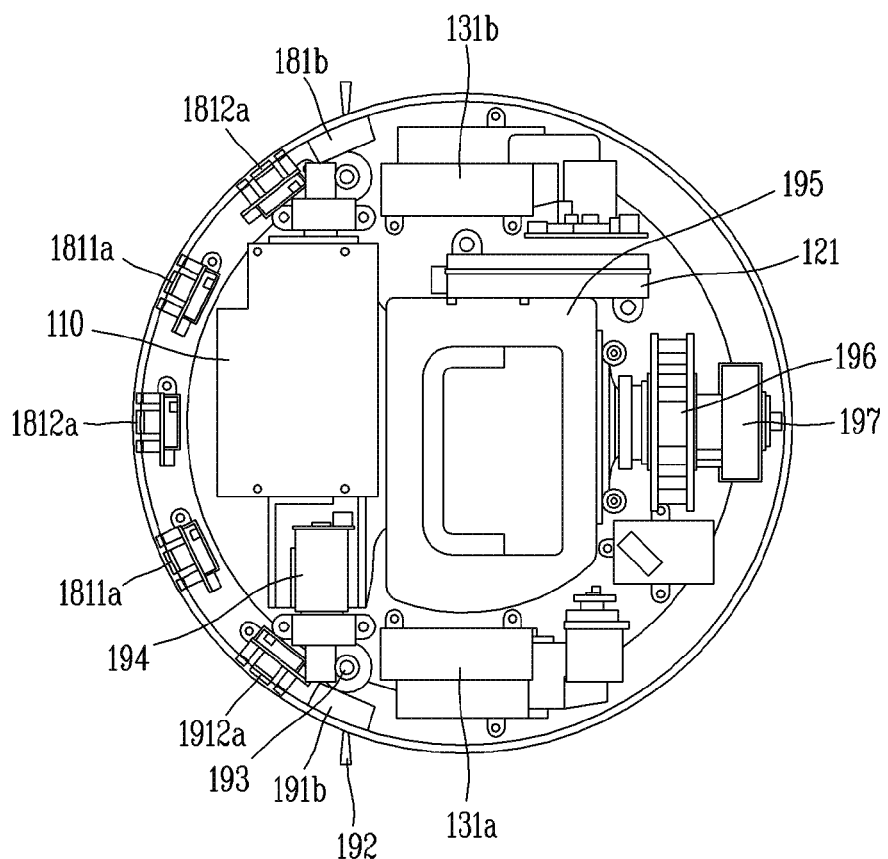
[Fig. 5]
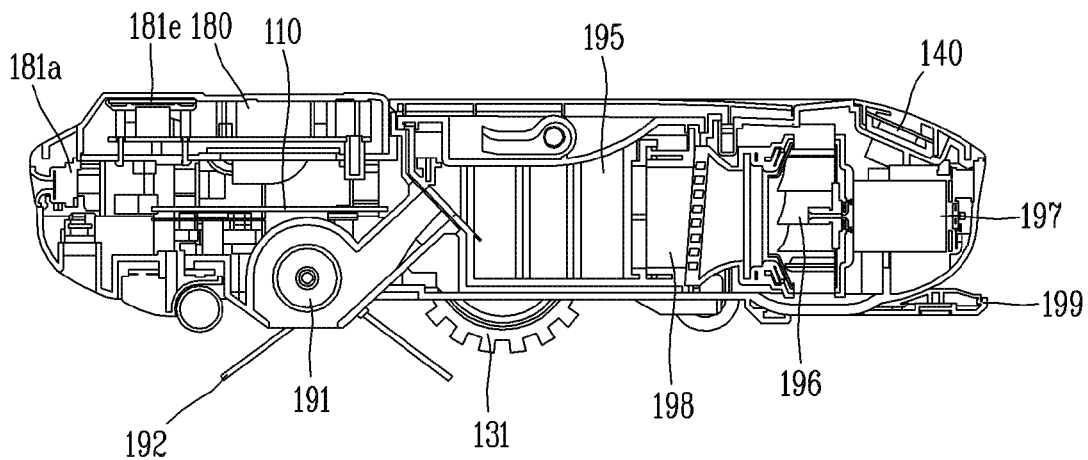

[Fig. 6]
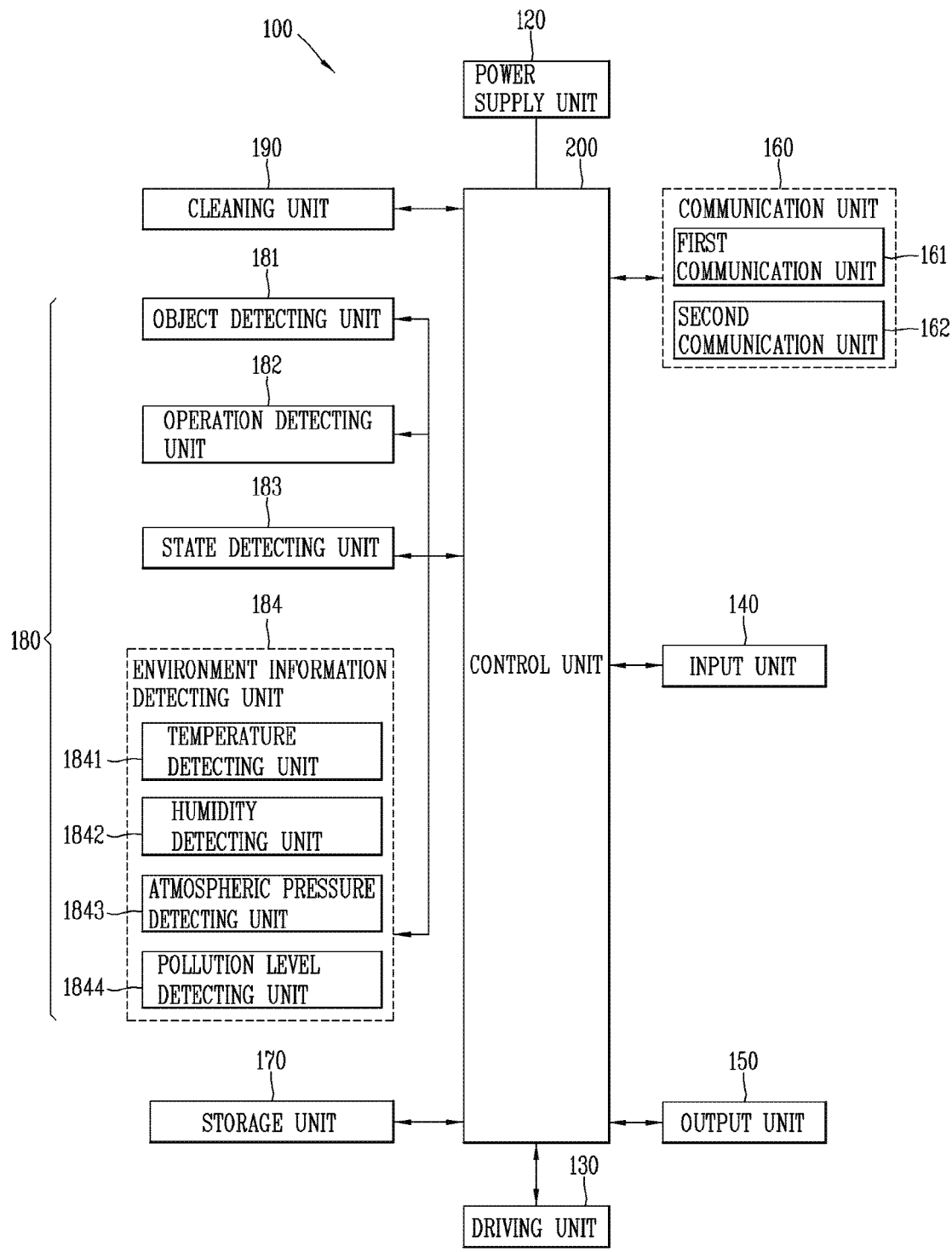

[Fig. 7]
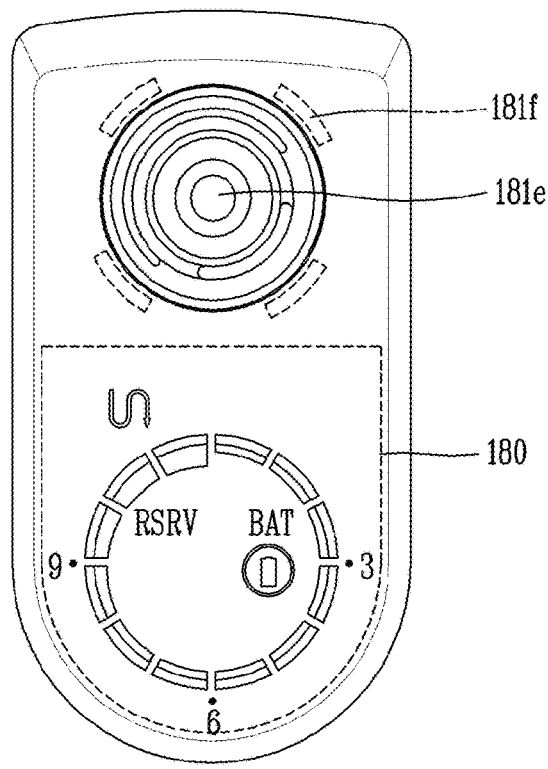
[Fig. 8a]
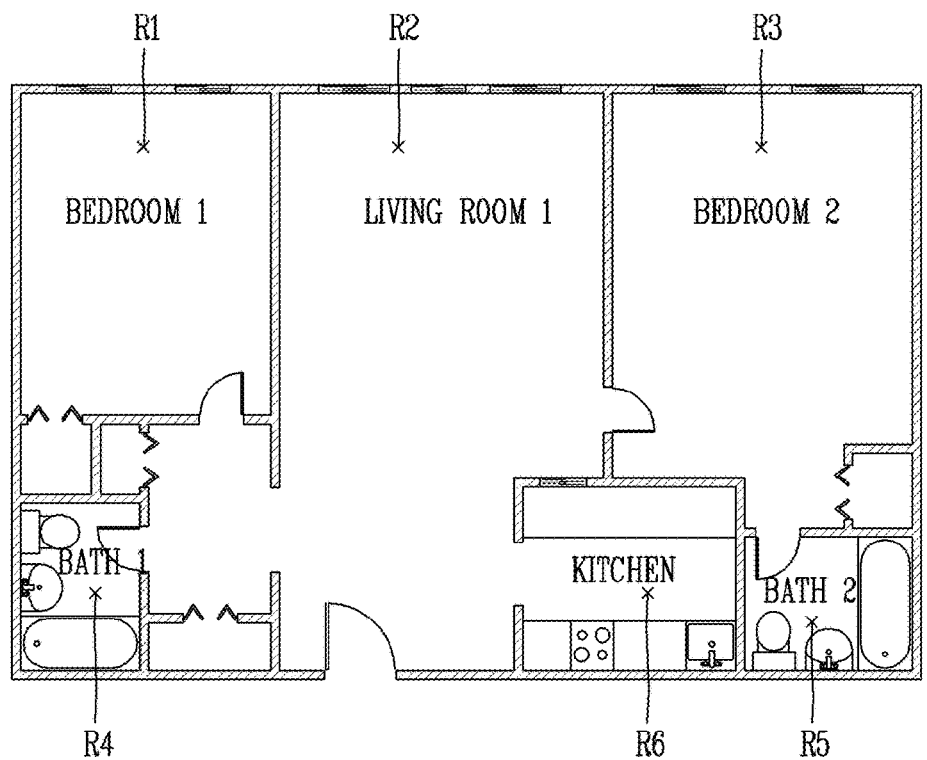

[Fig. 8b]
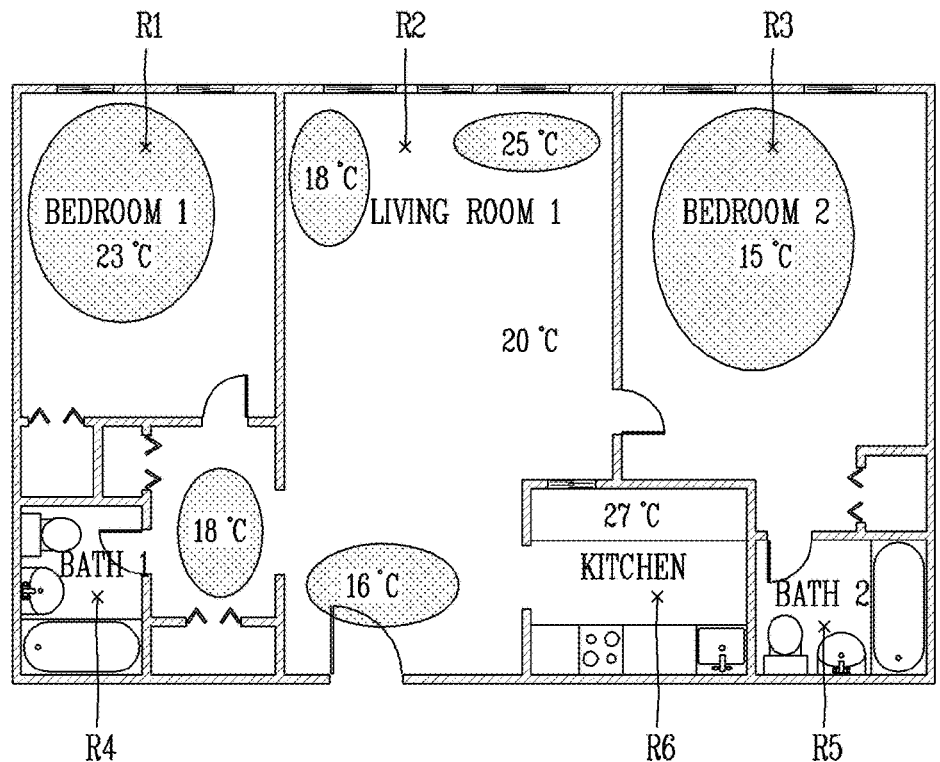
[Fig. 8c]
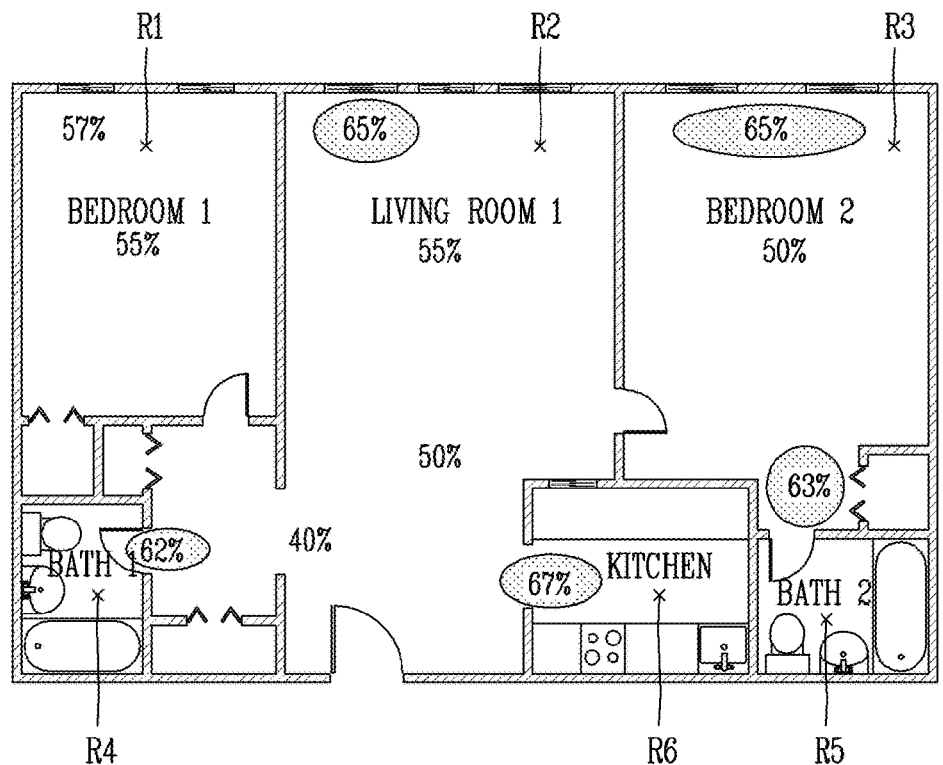

[Fig. 8d]
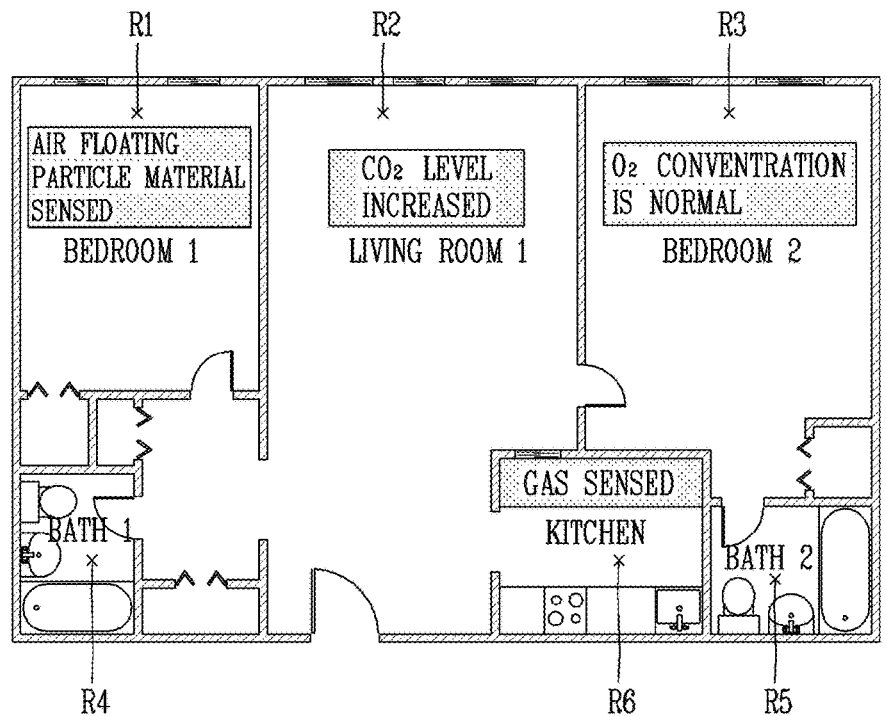
[Fig. 9a]
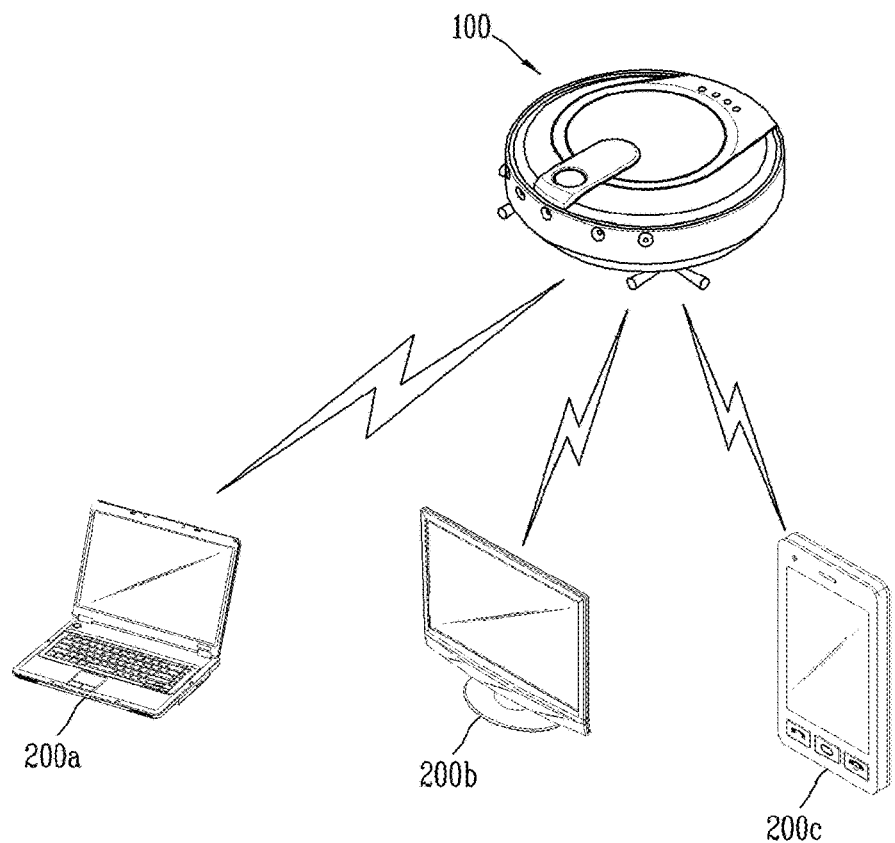

[Fig. 9b]
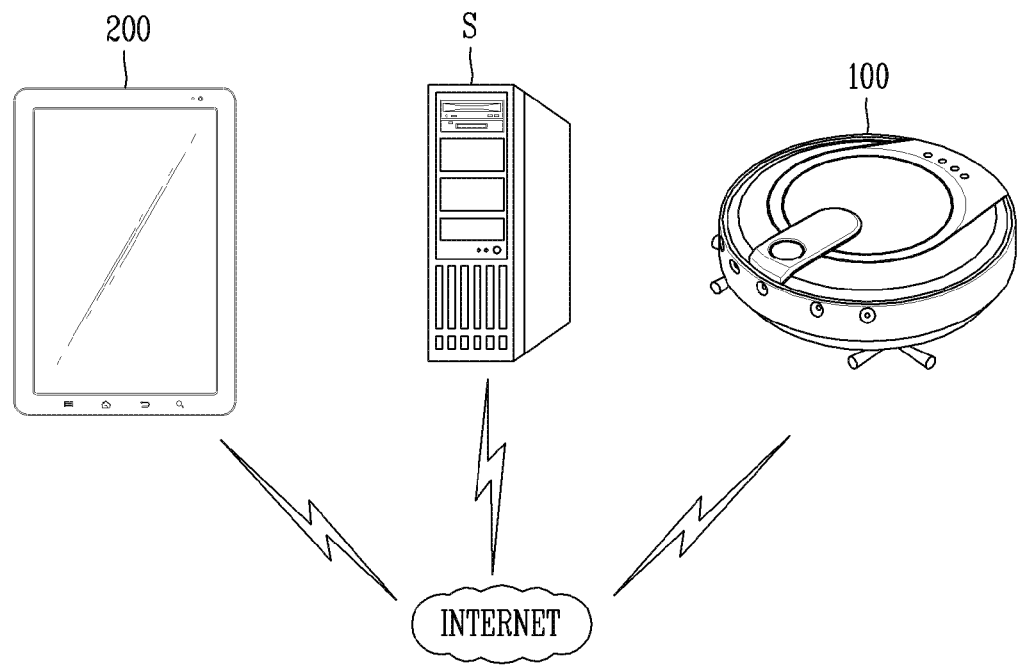
[Fig. 9c]
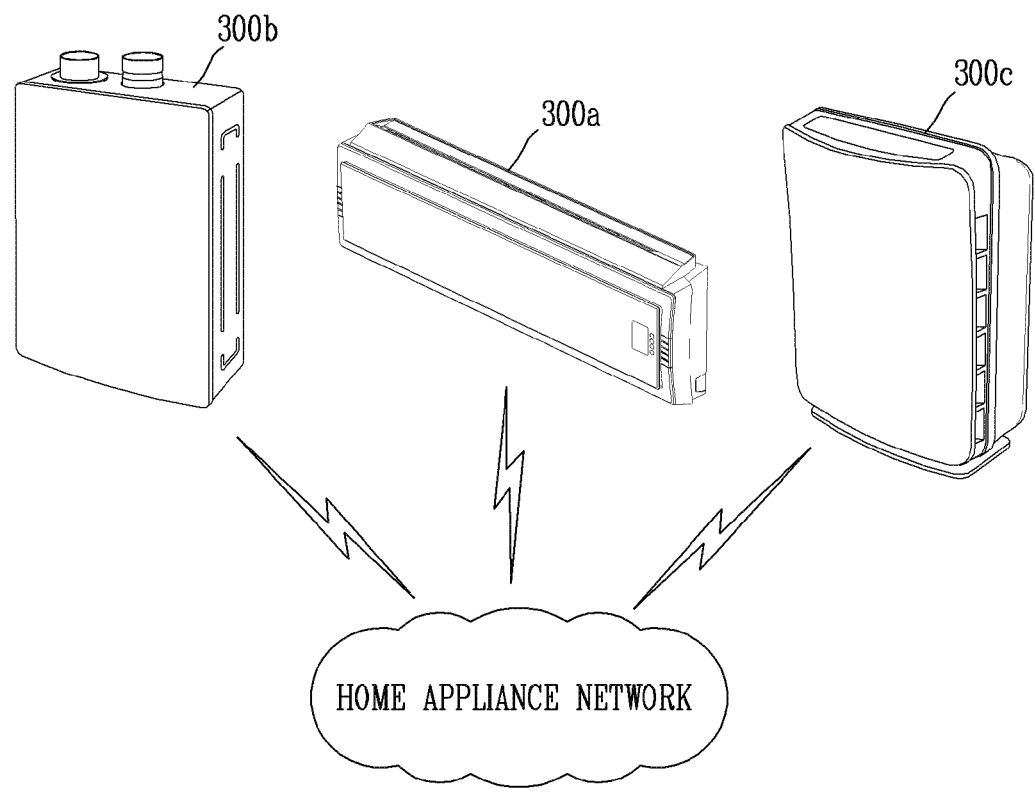

[Fig. 10a]
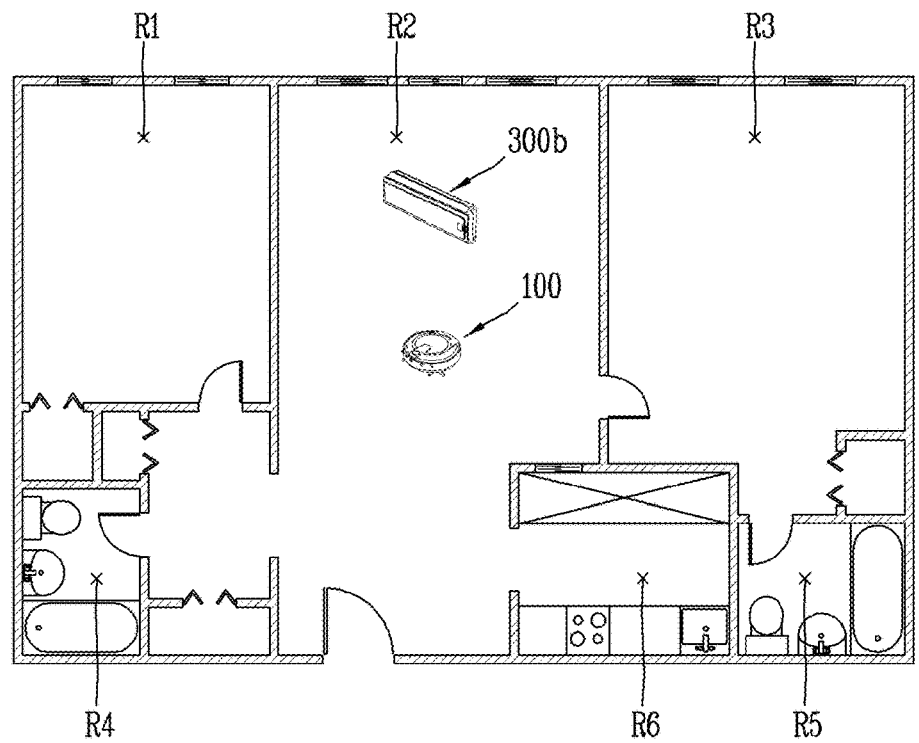
[Fig. 10b]
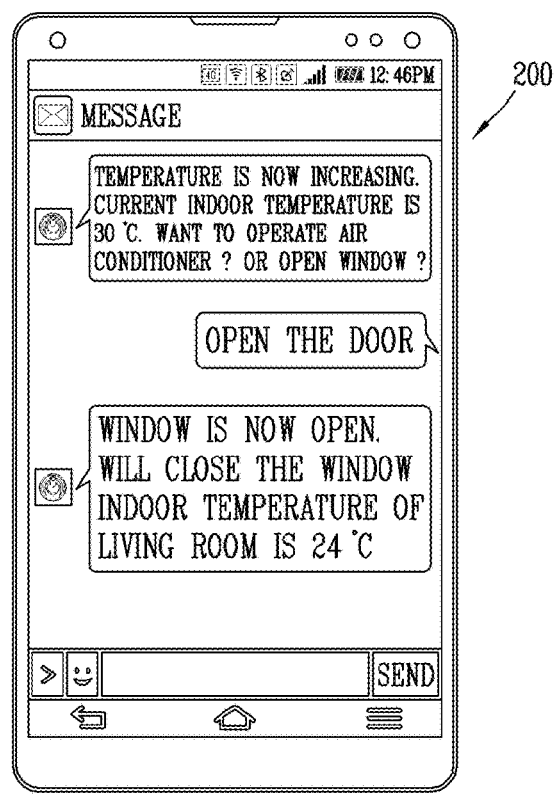

[Fig. 11]
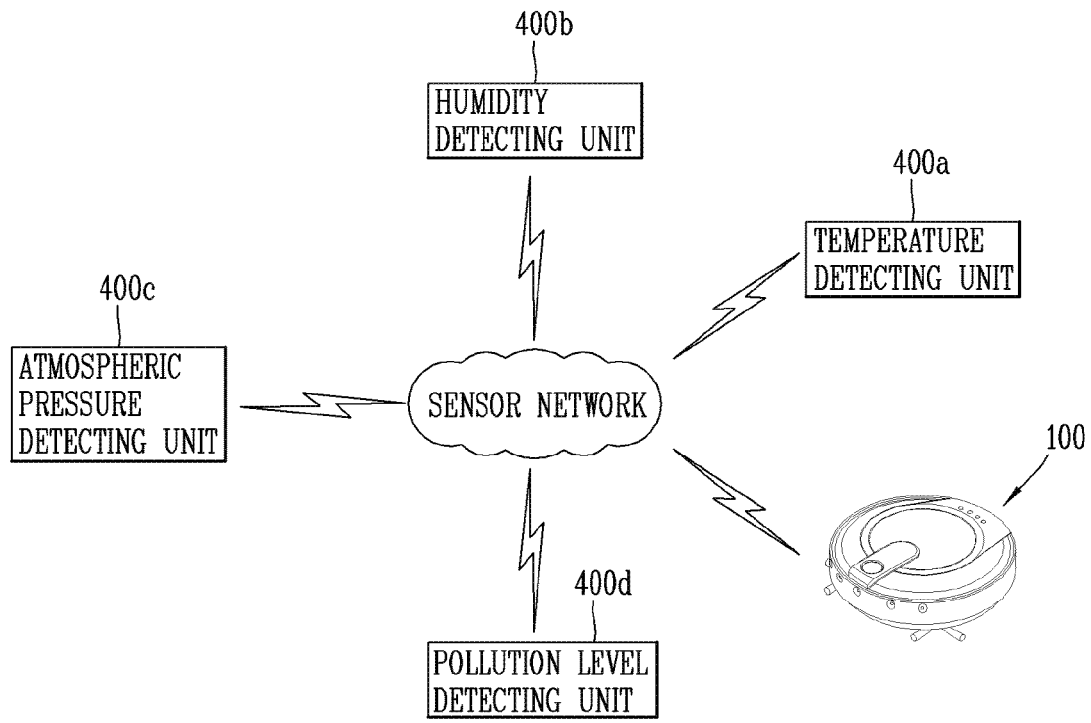
[Fig. 12]
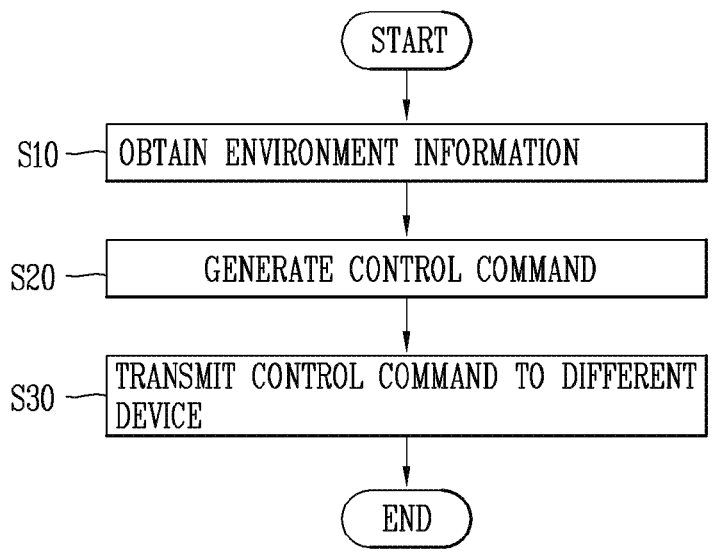

[Fig. 13]
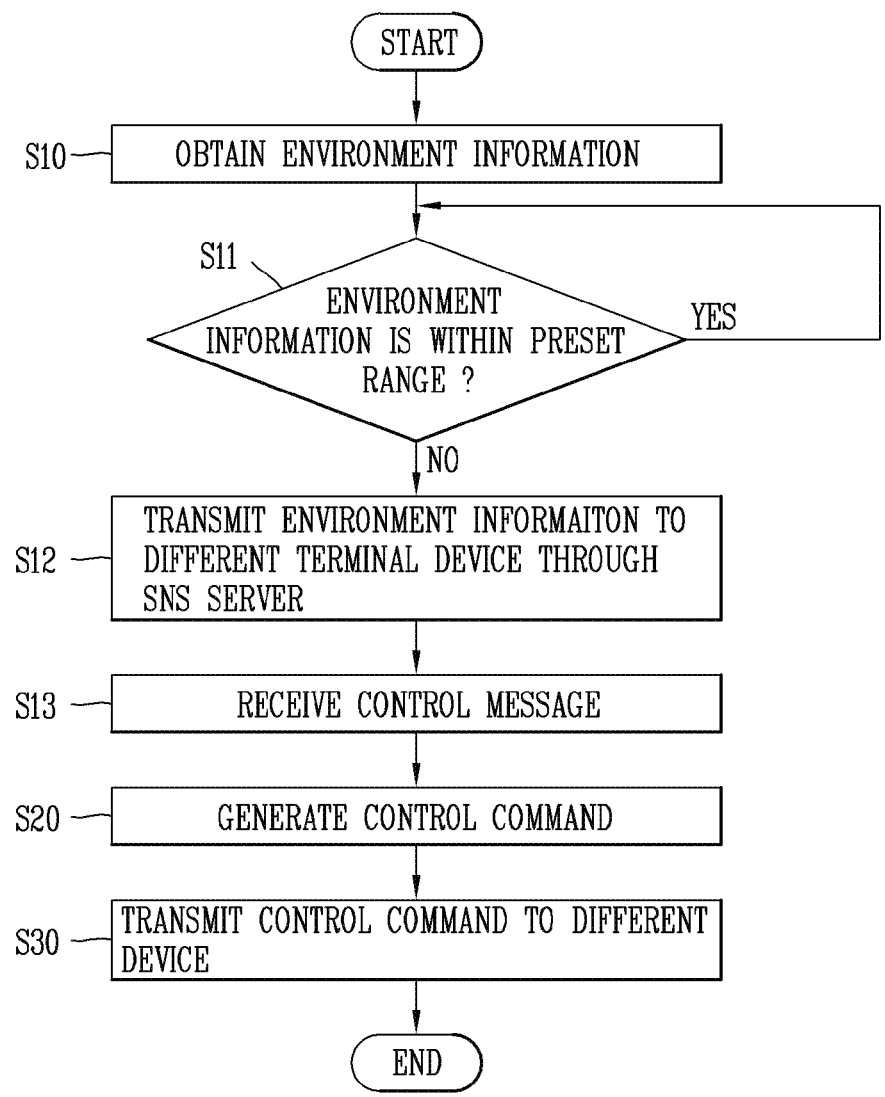

[Fig. 14]
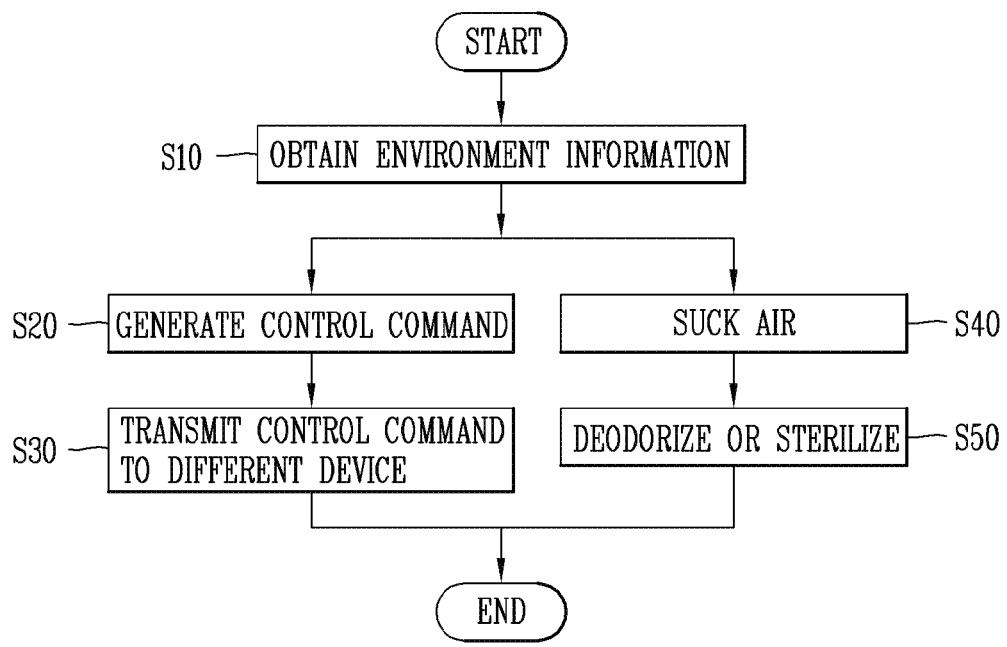

ROBOT CLEANER, REMOTE CONTROL SYSTEM INCLUDING THE SAME, AND CONTROL METHOD THEREOF

CROSS-REFERENCE TO RELATED PATENT APPLICATIONS

This application is a U.S. National Stage Application under 35 U.S.C. § 371 of PCT Application No. PCT/KR2016/001489, filed Feb. 15, 2016, which claims priority to Korean Patent Application No. 10-2015-0023612, filed Feb. 16, 2015, whose entire disclosures are hereby incorporated by reference.

TECHNICAL FIELD

The present disclosure relates to a robot cleaner, and more particularly, to a robot cleaner for obtaining environment information within a cleaning area and controlling the same, a remote control system including the same, and a method for controlling a robot cleaner.

BACKGROUND ART

In general, a robot has been developed for an industrial purpose and has been in charge of part of factory automation. Recently, robot-applied fields have further extended to develop medical robots or aerospace robots, and home robots that may be used in general houses have also been made.

A typical example of home robots is a robot cleaner, which is a sort of a home appliance for performing cleaning by sucking ambient dust or foreign objects, while traveling in a predetermined area. Such a robot cleaner includes a generally rechargeable battery and has an obstacle sensor capable of avoiding an obstacle during traveling so that the robot cleaner may perform cleaning, while traveling.

Recently, beyond performing cleaning while robot cleaners are simply autonomously traveling in a cleaning area, research into utilization of robot cleaners in various fields such as healthcare, smart home, remote control, and the like, has been actively conducted.

DISCLOSURE OF INVENTION

Technical Problem

Therefore, an object of the present invention is to provide a robot cleaner capable of sensing an environment (for example, a temperature, humidity, atmospheric pressure, a pollution level, and the like) in a cleaning area and controlling the same, a remote control system including the robot cleaner, and a method of controlling a robot cleaner.

Solution to Problem

According to an aspect of the present invention, there is provided a robot cleaner including: an environment information detecting unit configured to obtain environment information regarding at least a portion of a cleaning area; a first communication unit configured to transmit and receive data to and from a different device positioned within the cleaning area; and a control unit configured to generate a control command regarding the different device in order to adjust the obtained environment information.

According to an embodiment of the present disclosure, the robot cleaner may further include: a storage unit configured to store the environment information and corresponding position information.

According to an embodiment of the present disclosure, the robot cleaner may further include: a storage unit configured to store position information regarding the different device, wherein the control unit may generate a control command regarding a different device at a position corresponding to the environment information.

According to an embodiment of the present disclosure, the environment information detecting unit may detect at least one of a temperature, humidity, atmospheric pressure, and an air pollution level around the robot cleaner.

According to an embodiment of the present disclosure, the robot cleaner may further include: a second communication unit configured to transmit and receive data to and from a terminal device generating a control command regarding the different device, wherein the control unit may transmit the environment information to the terminal device.

According to an embodiment of the present disclosure, when the environment information is outside of a preset range, the second communication unit may transmit the environment information to the terminal device through an SNS server and receive a control message regarding the different device through the SNS server, and the control unit may generate a control command regarding the different device on the basis of the control message.

According to an embodiment of the present disclosure, the control unit may further include: a storage unit configured to store environment information for a predetermined period of time, wherein the control unit may calculate a predetermined pattern regarding a time range in which the environment information is outside of a preset range, and generate a control command regarding the different device before the time range estimated on the basis of the predetermined pattern is reached.

According to an embodiment of the present disclosure, the robot cleaner may further include: an obstacle detecting unit configured to detect an obstacle of the cleaning area using at least one sensor; and a position recognizing unit configured to recognize a position of the robot cleaner using at least one sensor, wherein the control unit may generate a cleaning map regarding the cleaning area on the basis of information regarding the obstacle detected by the obstacle detecting unit and information regarding the position recognized by the position recognizing unit.

According to an embodiment of the present disclosure, the robot cleaner may further include: a storage unit configured to store the environment information and corresponding position information, wherein the position information may be information indicating a region divided on the basis of the obstacle in the cleaning area.

According to an embodiment of the present disclosure, the environment information detecting unit may include an air sensor configured to sense dust in the air or a material included in the air.

According to an embodiment of the present disclosure, the robot cleaner may further include: an air purifying unit configured to deodorize or sterilize sucked air, wherein the control unit may purify the sucked air using the air purifying unit on the basis of pollution information sensed by the air sensor.

According to an embodiment of the present disclosure, the robot cleaner may further include: a storage unit configured to store position information regarding the different device, wherein the control unit may recognize environment information of a position corresponding to the position information of the different device as environment information detected by the different device.

According to an embodiment of the present disclosure, the environment information may include at least one of a temperature, humidity, atmospheric pressure, and an air pollution level.

According to an embodiment of the present disclosure, the robot cleaner may further include: an air purifying unit configured to deodorize or sterilize sucked air, wherein the control unit may purify the sucked air using the air purifying unit on the basis of an air pollution level detected by the different device.

According to an embodiment of the present disclosure, the robot cleaner may further include: an output unit configured to output the environment information to the outside in a visual or audible manner.

According to an embodiment of the present disclosure, when the environment information is outside of a preset range, the control unit may output an alarm signal through the output unit.

According to another aspect of the present invention, there is provided a remote control system of a robot cleaner, including: the foregoing robot cleaner; and a terminal device configured to generate a control command regarding the robot cleaner and the different device.

According to another aspect of the present invention, there is provided a method of controlling a robot cleaner, including: obtaining environment information regarding at least a portion of a cleaning area; generating a control command regarding a different device positioned within the cleaning area in order to adjust the obtained environment information; and transmitting the control command to the different device.

According to an embodiment of the present disclosure, the method may further include: when the environment information is outside of a preset range, transmitting the environment information to a terminal device through an SNS server; and receiving a control message regarding the different device from the terminal device through the SNS server, wherein, in the generating of the control command, the control command regarding the different device may be generated on the basis of the control message.

According to an embodiment of the present disclosure, in the obtaining of the environment information, an air sensor may sense dust in the air or a material included in the air, wherein the method may further include: deodorizing or sterilizing sucked air on the basis of pollution information sensed by the air sensor.

According to another aspect of the present invention, there is provided a computer-readable recording medium recording a computer program for executing the method of controlling a cleaner.

Advantageous Effects of Invention

In the robot cleaner, the remote control system including the same, and the control method thereof according to embodiments of the present invention, environment information regarding a cleaning area may be adjusted through the robot cleaner and/or a different device such as a home appliance by using information obtained through various sensors provided in the main body of the robot cleaner and a cleaning map generated for the cleaning area, to thereby provide an optimal environment to a user.

Also, environment information regarding a cleaning area may be adjusted through the robot cleaner and/or a different device such as a home appliance, and the robot cleaner may receive a corresponding control command may in the form of a message from a terminal device.

Also, by adjusting environment information regarding a cleaning area in advance through a different device before the environment information moves out of a preset range, an optimal environment regarding the cleaning area may be provided to the user.

Also, in order to purify air in at least a portion of the cleaning area, air purification may be performed on the entirety of the cleaning area by utilizing the air purifying unit included in the main body of the robot cleaner 100, without transmitting an air conditioning control command to a different device, and air purification may be performed by actively sucking ambient air by utilizing a suction motor for sucking ambient air of the robot cleaner.

Also, the robot cleaner may not need to include all the sensors corresponding to environment information to obtain the environment information, and even though any one sensor has an error, environment information intended to be obtained from the erroneous sensor may be received from a different device, thus obtaining environment information.

BRIEF DESCRIPTION OF DRAWINGS

FIG. 1 is a perspective view illustrating an external appearance of a robot cleaner according to an embodiment of the present disclosure.

FIG. 2 is a front view illustrating an external appearance of a robot cleaner according to an embodiment of the present disclosure.

FIG. 3 is a rear view illustrating an external appearance of a robot cleaner according to an embodiment of the present disclosure.

FIG. 4 is a cross-sectional view illustrating the interior of a robot cleaner according to an embodiment of the present disclosure.

FIG. 5 is a side cross-sectional view illustrating the interior of a robot cleaner according to an embodiment of the present disclosure.

FIG. 6 is a block diagram illustrating a configuration of a robot cleaner according to an embodiment of the present disclosure.

FIG. 7 is an enlarged view illustrating an output unit of a robot cleaner according to an embodiment of the present disclosure.

FIG. 8A is a view illustrating a cleaning map stored in a robot cleaner according to an embodiment of the present disclosure.

FIG. 8B is a view illustrating a temperature distribution sensed by a temperature detecting unit with respect to a cleaning area according to an embodiment of the present disclosure.

FIG. 8C is a view illustrating a humidity distribution sensed by a humidity detecting unit with respect to a cleaning area according to an embodiment of the present disclosure.

FIG. 8D is a view illustrating air pollution level information sensed by an environment information detecting unit with respect to a cleaning area according to an embodiment of the present disclosure.

FIG. 9A is a conceptual view of a remote control system of a robot cleaner according to an embodiment of the present disclosure.

FIG. 9B is a conceptual view illustrating a state in which a robot cleaner, a terminal device, and an SNS server are connected via a network according to an embodiment of the present disclosure.

FIG. 9C is a conceptual view illustrating a configuration in which home appliances form a home appliance network according to an embodiment of the present disclosure.

FIG. 10A is a view illustrating a state in which a robot cleaner and a home appliance are disposed in a cleaning area according to an embodiment of the present disclosure.

FIG. 10B is a view illustrating a screen output by a terminal device when a robot cleaner is connected to the terminal device through an SNS server according to an embodiment of the present disclosure.

FIG. 11 is a conceptual view illustrating a state in which sensors included in a robot cleaner and/or home appliances form a sensor network according to an embodiment of the present disclosure.

FIG. 12 is a flow chart illustrating a sequential process of a method of controlling a robot cleaner according to an embodiment of the present disclosure.

FIG. 13 is a flow chart illustrating a sequential process of a method of controlling a robot cleaner according to another embodiment of the present disclosure.

FIG. 14 is a flow chart illustrating a sequential process of a method of controlling a robot cleaner according to another embodiment of the present disclosure.

BEST MODE FOR CARRYING OUT THE INVENTION

Hereinafter, embodiments of the present disclosure will be described in detail with reference to the accompanying drawings. The terminology used herein is for the purpose of describing particular embodiments only and is not intended to be limiting of the invention. Unless otherwise defined, all terms used herein have the same meaning as commonly understood by one of ordinary skill in the art to which this invention pertains, and should not be interpreted as having an excessively comprehensive meaning nor as having an excessively contracted meaning. If technical terms used herein is erroneous that fails to accurately express the technical idea of the present invention, it should be replaced with technical terms that allow the person in the art to properly understand. The general terms used herein should be interpreted according to the definitions in the dictionary or in the context and should not be interpreted as an excessively contracted meaning.

First Embodiment

FIGS. 1 through 4 are a perspective view, a front view, a rear view, and a cross-sectional view of a robot cleaner according to an embodiment of the present disclosure.

A robot cleaner 100 may include a cleaning unit (please refer to FIG. 6) for sucking dust or foreign objects to perform cleaning.

The cleaning unit 190 includes an agitator 191 rotatably installed in a lower portion of a main body of the robot cleaner, and a side brush 192 rotating about a rotational shaft of the main body of the robot cleaner in a vertical direction to clean the corner, a nook, and the like, of a cleaning region such as a wall surface, or the like.

The agitator 191 rotates about an axis of the main body of the robot cleaner in a horizontal direction, to make dust of the floor, the carpet, and the like, float in the air. A plurality of blades are provided in a spiral direction on an outer circumferential surface of the agitator 191. A brush may be provided between the spiral blades. Since the agitator 191 and the side brush 192 rotate about different axes, the robot cleaner 100 generally needs to have a motor for driving the agitator 191 and a motor for driving the side brush 192.

Alternatively, as illustrated in FIGS. 2 and 3, the side brush 192 is disposed on both sides of the agitator 191 and an motor unit 193 (that is, a motor) is provided between the agitator 191 and the side brush 192 to transmit rotary power of the agitator 191 to the side brush 192, such that both the agitator 191 and the side brush 192 may be driven by using a single brush motor 194. In this case, as the motor unit, a worm and a worm gear may be used, or a belt may be used.

As illustrated in FIGS. 4 and 5, the cleaning unit 190 may include a dust container 195 storing collected dust, a sucking fan 196 providing power to suck dust in a cleaning region, and a sucking motor 197 rotating the sucking fan 196 to suck air, thereby sucking dust or foreign objects.

The sucking fan 196 includes a plurality of blades for making air flow, and a member formed to have an annular shape on an outer edge of an upper stream of the plurality of blades to connect the plurality of blades, and guiding air introduced in a direction of a central axis of the sucking fan 196 to flow in a direction perpendicular to the central axis.

Here, the cleaning unit 190 may further include a filter 198 having a substantially rectangular shape and filtering out filth or dust in the air.

The filter 198 may include a first filter and a second filter as needed, and a bypass filter may be formed in a body forming the filter. The first filter and the second filter may be a mesh filter or a high efficiency particulate arresting (HEPA) filter. The first filter and the second filter may be formed of either non-woven cloth or a paper filter, or both the non-woven cloth and the paper filter may be used together.

A control unit 110 may detect a state of the dust container 195. In detail, the control unit 110 may detect an amount of dust collected in the dust container 195 and detect whether the dust container 195 is installed in the robot cleaner 100 or whether the dust container 195 has been separated from the robot cleaner 100. In this case, the control unit may sense a degree to which dust is collected in the dust container by inserting a piezoelectric sensor, or the like, into the dust container. Also, an installation state of the dust container may be sensed in various manners. For example, as a sensor for sensing whether the dust container is installed, a microswitch installed to be turned on and off on a lower surface of a recess in which the dust container is installed, a magnetic sensor using a magnetic field of a magnet, an optical sensor including a light emitting unit and a light receiving unit, and receiving light, and the like, may be used. The magnetic sensor may include a sealing member formed of a synthetic rubber material in portion where magnet is bonded.

Also, the cleaning unit 190 may further include a rag plate 199 detachably attached to a lower portion of the main body of the robot cleaner. The rag plate 199 may include a detachably attached rag, and the user may separate the rag to wash or replace it. The rag may be installed in the rag plate in various manners, and may be attached to the rag plate 199 by using a patch called Velcro. For example, the rag plate 199 is installed in the main body of the robot cleaner 100 by magnetism. The rag plate 199 includes a first magnet and the main body of the cleaner may include a metal member or a second magnet corresponding to the first magnet. When the rag plate 199 is normally positioned on the bottom of the main body of the robot cleaner 100, the rag plate 199 is fixed to the main body of the robot cleaner 100 by the first magnet and a metal member or the first magnet and the second magnet.

The robot cleaner 100 may further include a sensor sensing whether the rag plate 199 is installed. For example, the sensor may be a reed switch operated by magnetism, or may be a hall sensor. For example, the reed switch may be provided in the main body of the robot cleaner 100, and when the rag plate 199 is coupled to the main body of the robot cleaner 100, the reed switch may operate to output an installation signal to the control unit 110.

Meanwhile, as illustrated in FIG. 2, the robot cleaner 100 may include main wheels 131*a* and 131*b* provided on the left and right sides of a lower portion thereof to allow the main body of the robot cleaner 100 to move. A driving unit 130 may be connected to the left and right main wheels 131*a* and 131*b* and include a motor (for example, a wheel motor) for rotating the main wheels 131*a* and 131*b*. By rotating the motor, the main body of the robot cleaner 100 may be rotated or moved.

Here, a plurality of wheel motors may be provided to be connected to the main wheels 131*a* and 131*b*, and here, the plurality of wheel motors may independently operate such that the main wheels 131*a* and 131*b* may be individually controlled.

Also, the robot cleaner 100 may further include one or more auxiliary wheels 132*a*, 132*b*, and 132*c* provided on the rear surface thereof. The auxiliary wheels 132*a*, 132*b*, and 132*c* may support the main body of the robot cleaner 100 and minimizes frictional contact between a lower surface of the main body of the robot cleaner 100 and a floor (the surface to be cleaned) to assist the robot cleaner 100 to smoothly move.

Also, a handle may be installed in an edge of a lower portion of the main body of the robot cleaner 100, for example, on both sides of the main wheels 131*a* and 131*b*.

FIG. 6 is a block diagram illustrating a configuration of the robot cleaner according to an exemplary embodiment of the present disclosure.

As illustrated in FIG. 6, the robot cleaner 100 according to an exemplary embodiment of the present disclosure may include a control unit 110, a power supply unit 120, an environment information detecting unit 184, a driving unit 130, an input unit 140, an output unit 150, a communication unit 160, a storage unit 170, a detecting unit 180, and a cleaning unit 190. Here, the robot cleaner 100 may include at least one of these elements or combinations thereof.

Here, the components illustrated in FIG. 6 are not essential and a robot cleaner including greater or fewer components may be implemented. Hereinafter, the components will be described.

First, the power supply unit 120 includes a battery 121 that may be charged by external commercial power and supply power to the interior of the robot cleaner 100. The power supply unit 120 may supply driving power to each of the components included in the robot cleaner to provide operation power required for the robot cleaner 100 to travel (or move or run) or perform cleaning.

Here, the control unit 110 detects a remaining capacity of power of the battery 121, and when the remaining capacity of power is insufficient, the control unit 110 controls the robot cleaner 100 to a recharging base connected to an external commercial power, and the battery 121 may be charged upon receiving a charge current from the recharging base. The battery 121 may be connected to a battery sensing unit and a remaining battery capacity and a charging state thereof may be transmitted to the control unit 110. As illustrated in FIG. 7, the output unit 150 may display a remaining battery capacity on a screen by the control unit 110.

The battery 121 may be positioned in a lower portion of the center of the robot cleaner 100, and as illustrated in FIG. 4, the battery 121 may be positioned on one of left and right side such that the dust container 195 is positioned in the lowermost portion of the main body of the robot cleaner 100. In the latter case, the robot cleaner 100 may further include a balance weight (or a counter weight) in order to resolve weight unbalance of the battery 121.

Meanwhile, since the driving unit 130 includes a motor and drives the motor, the driving unit 130 may rotate the left and right main wheels 131*a* and 131*b* in both directions to rotate or move the main body of the robot cleaner 100. Details thereof are the same as those described above, and thus, here, a detailed description thereof will be omitted.

Meanwhile, the input unit 140 receives various control commands with respect to the robot cleaner 100 from a user. The input unit 14 may include one or more buttons. For example, the input unit 140 may include an OK button, a setting button, and the like. The OK button may be a button for receiving a command for ascertaining sensing information, obstacle information, position information, a cleaning region, or a cleaning map, and the setting button may be a button for receiving a command for setting the foregoing information from the user.

Also, the input unit 140 may include an input resetting button for canceling a previous user input and receiving a user input again, a deletion button for deleting a preset user input, a cleaning start button, a cleaning stop button, a reservation button for setting or deleting reservation information, a button for setting or changing a cleaning mode, a button for receiving a command for returning to the recharging base, and the like.

Also, as illustrated in FIGS. 1 and 5, the input unit 140 may be a hard key, a soft key, a touch pad, and the like, and may be installed in an upper portion of the robot cleaner 100. Also, the input unit 140 may have a form of a touch screen together with the output unit 150.

Meanwhile, as illustrated in FIG. 1, the output unit 150 may be installed in an upper portion of the robot cleaner 100. Of course, the installation position and installation form may vary. For example, as illustrated in FIG. 7, the output unit 150 may display a cleaning scheme or a traveling scheme such as reservation information, a battery state, intensive cleaning, space expansion, zigzag operation, and the like, on a screen.

Also, the output unit 150 may output internal state information of the robot cleaner 100 detected by the detecting unit 180, for example, the current state of each component included in the robot cleaner and the current cleaning state. Also, the output unit 150 may display external state information detected by the detecting unit 180, for example, obstacle information, position information, a cleaning region, a cleaning map, and the like, on the screen. The output unit 150 may be formed as any one device among a light emitting diode (LED), a liquid crystal display (LCD), a plasma display panel (PDP), and an organic light emitting diode (OLED).

The output unit 150 may further include an audio output unit acoustically outputting an operation process or an operation result of the robot cleaner 100 performed by the control unit 110. For example, the output unit 150 may output a warning sound (or an alarm sound) to the outside according to a warning signal generated by the control unit 110.

Here, the audio output unit may be a unit for outputting a sound, such as a beeper, a speaker, and the like, and the output unit 105 may output a sound through the audio output unit using audio data or message data having a predetermined pattern stored in the storage unit 170.

Thus, the robot cleaner according to an embodiment of the present disclosure may output a cleaning map and/or environment information regarding a cleaning area on a screen or as a sound through the output unit 150. Also, according to another embodiment of the present disclosure, the robot cleaner may transmit the cleaning map and/or environment information to a terminal device 200 through a second communication unit 162 such that the screen or the sound to be output through the output unit 150 is output by the terminal device 200.

Accordingly, as described hereinafter, when the environment information detected by the environment information detecting unit 184 is outside of a preset range, the control unit 110 may output an alarm signal in a visual or audible manner through the output unit 150. Also, according to another embodiment of the present disclosure, in a case in which the control unit 110 determines that there is environment information outside of the preset range, the control unit 110 may transmit a corresponding alarm signal to the terminal device 200 and the terminal device 200 which has received the alarm signal may output the alarm signal in a visual or audible manner.

Meanwhile, the communication unit 160 may be connected to the terminal device 200 and/or a different device (in the present disclosure, it will be mixedly used together with a term of "home appliance") positioned within a cleaning area through one of wired, wireless, and satellite communication schemes to transmit and receive a signal and data.

As illustrated in FIG. 6, the communication unit 160 may include a first communication unit 161 and a second communication unit 162. The first communication unit 161 and the second communication unit 162 are divided according to counterpart nodes that transmit and receive data to and from the robot cleaner 100, and the first communication unit 161 and the second communication unit 162 may use the same communication scheme and may be implemented as a single module.

The first communication unit 161 may transmit and receive data to and from a different device positioned within the cleaning area. Here, the different device may be any device as long as it may be connected to a network and transmit and receive data. For example, as illustrated in FIG. 9C, the different device may be a device such as an air conditioning device 300a, a heating device 300b, an air purifying device 300c, a lamp (not shown), a TV (not shown), an automobile (not shown), and the like. Also, the different device may be a device (not shown) controlling a door, a window, a tap valve of a water tap, a gas valve, and the like. Also, the different device may be a sensor (not shown) sensing a temperature, humidity, atmospheric pressure, gas, and the like.

Thus, the control unit 110 may transmit a control signal to the different device through the first communication unit 161, and accordingly, the different device may operate according to the received control signal. For example, in a case in which the different device is the air conditioning device 300a, the air conditioning device 300a may perform cooling or heating on the cleaning area according to the control signal, and in a case in which the different device is a device for controlling a window, the device may open or close a window or open a window at a predetermined rate according to the control signal.

Also, the first communication unit 161 may receive various types of state information from the at least one different device positioned within the cleaning area. For example, the first communication unit 161 may receive a set temperature of the air conditioning device 300a, opening and closing information indicating whether a window is opened or closed or a degree of opening and closing the window, a current temperature of the cleaning area sensed by a temperature sensor, and the like.

Accordingly, the control unit 110 may generate a control signal regarding the different device according to the state information, a user input through the input unit 140, or a user input through the terminal device 200.

Here, as illustrated in FIG. 9C, in order to communicate with at least one different device 300, the first communication unit 161 may employ at least one communication scheme among wireless communication schemes such as radio frequency communication, Bluetooth, infrared data association (IrDA), a wireless local area network (LAN), ZigBee, and the like, and accordingly, the different device 300 and the robot cleaner 100 may form at least one network. Here, preferably, the network is the Internet.

The second communication unit 162 may receive a control signal from the terminal device 200. Thus, the control unit 110 may perform a command such as making a cleaning map, traveling within a cleaning area, performing cleaning, and the like, according to the control signal received through the second communication unit 162. For example, a control command that may be received from the user through the input unit 140 may be received from the terminal device 200 through the second communication unit 162, and the control unit 110 may perform the received control command. Also, the second communication unit 162 may transmit state information of the robot cleaner, obstacle information, position information, image information, a cleaning map, and the like, to the terminal device 200. For example, various types of information that may be output through the output unit 150 may be transmitted to the terminal device 200 through the second communication unit 162.

Here, as illustrated in FIG. 9A, in order to communicate with a terminal device such as a computer 200a such as a laptop computer, a display device 200b, and a mobile terminal (for example, a smartphone) 200c, and the like, the second communication unit 162 may employ at least one communication scheme among wireless communication schemes such as radio frequency (RF) communication, Bluetooth, infrared data association (IrDA), a wireless local area network (LAN), ZigBee, and the like, and accordingly, the different device 300 and the robot cleaner 100 may form at least one network. Here, preferably, the network is the Internet. For example, when the terminal device 200 is the mobile terminal 200c, the robot cleaner 100 may communicate with the terminal device 200 through the second communication unit 162 using a communication scheme available for the mobile terminal.

Meanwhile, the storage unit 170 stores a control program for controlling or driving the robot cleaner 100. The storage unit 170 may store audio information, image information, obstacle information, position information, a cleaning region, a cleaning map, and the like. Also, the storage unit 170 may store a cleaning scheme, a traveling method, and the like.

As the storage unit 170, a nonvolatile memory is mainly used. Here, the nonvolatile memory (NVM, or NVRAM) is a storage device capable of maintaining stored information even without power supply, which may be, for example, a ROM, a flash memory, a magnetic computer storage device (e.g., a hard disk, a diskette drive, a magnetic tape, etc.), an optical drive, a magnetic RAM, a PRAM, and the like.

Meanwhile, as illustrated in FIG. 6, the detecting unit 180 may include at least one among an object detecting unit 181, for detecting an external object, an operation detecting unit 182 for detecting an operation of the robot cleaner 100, and a state detecting unit 183 for detecting a state of units constituting the robot cleaner 100, and the environment information detecting unit 184.

The object detecting unit 181 may include at least one among an external signal sensor, a front sensor, a cliff sensor, a lower camera sensor, and an upper camera sensor.

The external signal sensor may sense an external signal of the robot cleaner 100. The external signal sensor may be, for example, an infrared sensor, an ultrasonic sensor, an RF sensor, and the like.

The robot cleaner 100 may receive a guide signal generated by the recharging base by using the external signal sensor and check a position and direction of the recharging base. Here, the recharging base may generate a guide signal indicating a direction and a distance such that the robot cleaner 100 may be returned. That is, the robot cleaner 100 may receive a signal transmitted from the recharging base, determine the current position, set a movement direction, and may be returned to the recharging base.

Also, the robot cleaner 100 may sense a signal generated by a remote control device such as a remote control unit, a terminal, and the like, by using the external signal sensor.

The external signal sensor may be provided on one side within the robot cleaner 100 or outside of the robot cleaner 100. For example, an infrared sensor 181b may be installed within the robot cleaner 100 or below the output unit 150, or as illustrated in FIG. 7, the infrared sensor 181f may be installed in the vicinity of the upper camera sensor 181e.

Meanwhile, the front sensor may be installed at a predetermined interval on a front side of the robot cleaner 100, specifically, along an outer circumferential surface of the side of the robot cleaner 100. The front sensor is positioned on at least one side of the robot cleaner 100 to sense an obstacle in front of the main body of the robot cleaner 100. The front sensor may sense an object, in particular, an obstacle, present in a direction in which the robot cleaner 100 moves, and transmit detection information to the control unit 110. That is, the front sensor may sense a protrusion present in a movement path of the robot cleaner 100, furnishings, furniture, a wall surface, a wall corner, and the like, in a house, and transmit corresponding information to the control unit 110.

The front sensor may be, for example, an infrared sensor, an ultrasonic sensor, an RF sensor, a geomagnetic sensor, and the like, and the robot cleaner 100 may use a type of sensor or two or more types of sensors together as the front sensor.

For example, in general, the ultrasonic sensor 181a may be mainly used to sense an obstacle in a remote area. The ultrasonic sensor 181a may include a transmission unit 1811a and a reception unit 1812a. The ultrasonic sensor 181a may determine whether an obstacle is present according to whether an ultrasonic wave radiated through the transmission unit 1811a is reflected by an obstacle, or the like, and received by the reception unit 1812, and calculate a distance to the obstacle by using an ultrasonic wave radiation time and an ultrasonic wave reception time.

As illustrated in FIG. 1 or 2, a plurality of ultrasonic sensors 181a (for example, five ultrasonic sensors) may be installed on an outer circumferential surface of a front side of the robot cleaner 100. Here, preferably, the transmission units 1811a and the reception units 1812a of the ultrasonic sensors 181a may be installed alternately on the front side of the robot cleaner 100.

Namely, the transmission units 1811a may be disposed to be spaced apart from the center of the front side of the main body of the robot cleaner 100, and in this case, one or two or more transmission units 1811a may be disposed between reception units 1812a to form a reception region of an ultrasonic signal reflected from the obstacle, or the like. Due to this disposition, a reception region may be expanded, while reducing the number of sensors. A transmission angle of ultrasonic waves may be maintained at an angle of a range which does not affect other signals to prevent a crosstalk phenomenon. Also, reception sensitivity of the reception units 1812a may be set to be different.

Also, the ultrasonic sensors may be installed upwardly at a predetermined angle such that ultrasonic waves generated by the ultrasonic sensors are output upwardly, and in this case, in order to prevent the ultrasonic waves from being radiated downwardly, a predetermined blocking member may be further provided.

Meanwhile, as mentioned above, two or more types of sensors may be used as the front sensors, and thus, one or more types of sensor among an infrared sensor, an ultrasonic sensor, and an RF sensor may be used as the front sensors.

For example, as illustrated in FIGS. 1 and 2, the front sensor may include an infrared sensor 181b as a different type of sensor, in addition to the ultrasonic sensor 181a.

As illustrated in FIGS. 2 and 4, the infrared sensor 181b may be installed on an outer circumferential surface of the robot cleaner 100 together with the ultrasonic sensor 181a. The infrared sensor 181b may also sense an obstacle present in front of or by the side of the robot cleaner 100 and transmits corresponding obstacle information to the control unit 110. That is, the infrared sensor 181b may sense a protrusion present in a movement path of the robot cleaner 100, furnishings, furniture, a wall surface, a wall corner, and the like, in a house, and transmit corresponding information to the control unit 110. Thus, the robot cleaner 100 may move in a cleaning area without colliding with an obstacle.

Meanwhile, as the cliff sensor, various types of optical sensors may be use, and the cliff sensor may sense an obstacle of the floor supporting the main body of the robot cleaner 100.

That is, the cliff sensor may be installed on a rear surface of the robot cleaner 100 and may be installed in different regions depending on a type of a robot cleaner. The cliff sensor may be positioned on a rear surface of the robot cleaner 100 to sense an obstacle on the floor. The cliff sensor may be an infrared sensor including a light emitting unit and a light receiving unit, an ultrasonic sensor, an RF signal, a position sensitive detector (PSD) sensor, and the like, like the obstacle sensor.

As illustrated in FIG. 3, for example, any one of cliff sensors 181c may be installed on the front side of the robot cleaner 100, and the other two cliff sensors may be installed on a relatively rear side.

The cliff sensors 181c illustrated in FIG. 3 may be disposed as follows. For example, for the purposes of description, the cliff sensor installed on the front side of the robot cleaner 100 will be referred to as a first sensor 1811c and the sensors installed on the relatively rear side will be referred to as second sensors 1812c. In general, the first sensor 1811c and the second sensors 1812c may be the same type of sensors, for example, PSD sensors, or the first sensor 1811c and the second sensors 1812c may be configured as different types of sensors.

Each of the PSD sensors detects a distance to an object of light by using a single p-n junction using semiconductor surface resistance. The PSD sensor includes a one-dimensional PSD sensor detecting light in only one axial direction and a two-dimensional PSD sensor detecting a light position on a plane. Both PSD sensors may have a pin photo diode structure. The PSD sensor is a type of infrared sensor which transmits an infrared ray to an obstacle and measures an angle between the infrared ray transmitted to the obstacle an infrared ray returned after being reflected from the obstacle, thus measuring a distance therebetween.

The PSD sensor includes a light emitting unit emitting infrared light to an obstacle and a light receiving unit receiving infrared light returned after being reflected from the obstacle. In general, the PSD sensor is formed as a module. In a case in which an obstacle is sensed by using the PSD sensor, a stable measurement value can be obtained regardless of difference in reflectivity or color of an obstacle.

The control unit 110 may measure an angle between an infrared light emitting signal irradiated by the first sensor 1811c toward the floor and a reflection signal received after being reflected from the obstacle to sense a cliff, and analyze a depth thereof.

Meanwhile, the control unit 110 may determine whether the robot cleaner 100 may be able to pass through the cliff according to states (height/depth) of the cliff sensed by using the first sensor 1811c and the second sensors 1812c. For example, the control unit 110 may determine whether a cliff is present and a depth of the cliff through the first sensor 1811c and only when a reflection signal is sensed by the second sensors 1812c, the control unit 110 allows the robot cleaner 100 to pass through the cliff.

In another example, the control unit 110 may determine whether the robot cleaner 100 is lifted according to a combination of sensing results of the first sensor 1811c and the second sensors 1812c.

Meanwhile, as illustrated in FIG. 3, the lower camera sensor 181d may be provided on a rear surface of the robot cleaner 100 and obtain image information regarding a lower side, namely, the floor (or a surface to be cleaned). The lower camera sensor 181d may also be called an optical flow sensor. The lower camera sensor 181d may convert an image of the lower side input through an image sensor provided therein to generate a predetermined format of image data. The generated image data may be stored in the storage unit 170

The lower camera sensor 181d may further include a lens (not shown) and a lens adjusting unit (not shown) for adjusting the lens (not shown). As the lens, a pan focus type lens having a short focal length and a deep depth is preferably used. The lens adjusting unit may include a predetermined motor and a moving unit to move the lens forwardly and backwardly and adjusts a position of the lens by using the motor and the moving unit.

Also, one or more light sources may be installed to be adjacent to an image sensor. One or more light sources irradiate light to a predetermined region of the floor captured by the image sensor. Namely, in a case in which the robot cleaner 100 moves a cleaning region along the floor, when the floor is smooth, a predetermined distance is maintained between the image sensor and the floor. On the other hand, in a case in which the robot cleaner 100 moves on the floor which is uneven, the image sensor may become away from the floor by a predetermined distance or greater due to depressions and protrusions and an obstacle of the floor. In this case, the one or more light sources may be controlled by the control unit 110 such that an amount of irradiated light can be adjusted. The light sources may be a light emitting device, for example, a light emitting diode (LED), or the like, whose amount of light can be adjusted.

The control unit 110 may detect a position of the robot cleaner 100 regardless of whether the robot cleaner 100 slides due to various factors, by using the lower camera sensor 181d. The control unit 110 may compare and analyze image data captured by the lower camera sensor 181d over time to calculate a movement distance and a movement direction, and calculate a position of the robot cleaner 100 on the basis of the calculated movement distance and the movement direction. By using the image information regarding the lower side of the robot cleaner 100 using the lower camera sensor 181d, the control unit 110 may perform correction resistant to sliding with respect to a position of the robot cleaner 100 calculated by other means.

Meanwhile, as illustrated in FIGS. 1 and 5, the upper camera sensor 181e may be installed to be oriented upwardly or forwardly of the robot cleaner 100 to capture an image of a surrounding area of the robot cleaner 100. In a case in which the robot cleaner 100 includes a plurality of upper camera sensors, the camera sensors may be formed on an upper portion or on a lateral surface of the robot cleaner 100 at a predetermined distance or at a predetermined angle.

The upper camera sensor 181e may include a lens for adjusting a focal point of a subject, an adjusting unit for adjusting the camera sensor, and a lens adjusting unit for adjusting the lens. As the lens, a lens having a wide angle of view may be used such that every surrounding region, for example, the entire region of the ceiling, may be imaged even in a predetermined position. For example, a lens having an angle equal to or greater than a predetermined angle of view, for example, equal to or greater than 160 degrees, may be used.

The control unit 110 may recognize a position of the robot cleaner 100 by sing image data captured by the upper camera sensor 181e, and create a cleaning map regarding the cleaning region. The control unit 110 may precisely recognize a position by using image data through an acceleration sensor, a gyro sensor, a wheel sensor, and the lower camera sensor and image data obtained by the upper camera sensor.

Also, the control unit 110 may generate a cleaning map as illustrated in FIG. 8A by using the obstacle information detected by the front sensor, the obstacle sensor, and the like, and the position recognized by the upper camera sensor 181e. Alternatively, the cleaning map may be received from the outside and stored in the storage unit 170, rather than being generated by the control unit 110.

Meanwhile, among terms used in this disclosure, "cleaning area" may be an aggregation of unit cleaning areas that may be formed by an obstacle such as a wall. That is, as illustrated in FIG. 8A, a cleaning area may include unit cleaning areas R1 to R6. Here, the control unit 110 may receive a mark (for example, a letter, a figure, and the like) indicating at least one cleaning area from the user through the input unit 140 or the second communication unit 162 and store the received mark in the storage unit 170. That is, as illustrated in FIG. 8A, the control unit 110 may receive "Bedroom 1" as a mark corresponding to the an area R1 among the cleaning areas, "Living Room" as a mark corresponding to an area R2, "Bedroom 2" as a mark corresponding to an area R3, "Bath 1" as a mark corresponding to an area R4, "Bath 2" as a mark corresponding to an area R5, and "Kitchen" as a mark corresponding to an area R6 from a user, and the storage unit 170 may store the marks. Accordingly, the output unit 150 may output the marks corresponding to the unit cleaning areas on the cleaning map, transmit a marks corresponding to the unit cleaning areas together when transmitting the cleaning map to the terminal device 200. Thus, when a control command is received from the user through the input unit 140 and/or the terminal device 200, the control command may be received on the basis of the mark indicating a target area in which a control operation is to be performed.

Meanwhile, the operation detecting unit 182 may include one or more of an acceleration sensor, a gyro sensor, and a wheel sensor, and detect an operation of the robot cleaner 100.

The acceleration sensor may detect a change in speed of the robot cleaner 100, for example, a change in a movement speed due to start, stop, a change in direction, collision with an object, and the like. The acceleration sensor may be attached to a position adjacent to the main wheel or an auxiliary wheel to detect sliding or idle rotation of the wheel. In this case, a speed is calculated by using the acceleration detected by the acceleration sensor, and a position of the robot cleaner 100 may be checked and corrected by comparing the calculated speed and a reference aped. However, in an exemplary embodiment of the present disclosure, the acceleration sensor is installed in the control unit 110 to sense a change in a speed of the robot cleaner 100 itself made in a cleaning mode and a traveling mode. That is the acceleration sensor may detect impulse according to a change in speed, and outputs a voltage value corresponding thereto. Thus, the acceleration sensor may serve as an electronic bumper.

Also, the gyro sensor senses a rotation direction and detects a rotation angle when the robot cleaner 100 moves according to an operation mode. The gyro sensor detects an angular velocity of the robot cleaner 100 and outputs a voltage value in proportion to the angular velocity. The control unit 110 may calculate a rotation direction and a rotation angle by using a voltage value output from the gyro sensor.

Also, the wheel sensor may be connected to main wheels on the left and right side to sense the revolution per minute (RPM) of each of the main wheels. The wheel sensor may be a rotary encoder. The rotary encoder may sense the RPM of each of the main wheels on the left and right side and output the same when the robot cleaner 100 moves in a traveling mode or a cleaning mode. The control unit 110 may calculate a rotation speed of the left and right wheels by using the RPM. Also, the control unit 110 may calculate a rotation angle of the robot cleaner 100 by using a difference in the RPMs of the left and right wheels sensed by the wheel sensor.

Meanwhile, the state detecting unit 183 includes sensors for detecting a state of each unit, such as sensors for detecting a state of the main wheels, a state of a wheel drop switch, a state of a suction motor, a state of an agitator, and the like. Also, the state detecting unit 183 may include a sensor for detecting a state of the dust container, a state of the battery, a state of the rag plate, and the like. Before a cleaning command is performed or while a battery of the robot cleaner is being charged, the control unit 110 may determine one of a state of the dust container, a state of the rag plate, and a state of the battery, or a combination of the states, and output the determination result through the output unit 150.

Meanwhile, the environment information detecting unit 184, which is a means for obtaining environment information regarding at least a portion of a cleaning area, may include at least one of a temperature detecting unit 1841 for detecting a temperature, a humidity detecting unit 1842 for detecting humidity, an atmospheric pressure detecting unit 1843 for detecting atmospheric pressure, and a pollution level detecting unit 1844 for detecting a pollution level of air.

The temperature detecting unit 1841 may include a temperature sensor installed in a predetermined position of the main body of the robot cleaner 100 to measure an ambient temperature (or a temperature of a surrounding environment). Here, the temperature sensor may measure an indoor temperature regarding at least one portion of a cleaning area and types of a temperature sensor are not particularly limited. Thus, the temperature detecting unit 1841 may measure an indoor temperature regarding at least a portion of the cleaning area and transmit a measured signal to the control unit 110.

The control unit 110 may sense a temperature of at least a portion of a cleaning area through the temperature detecting unit 1841. Also, the control unit 110 may store the sensed temperature of the at least a portion of the cleaning area and a position from which the temperature information was collected, together, in the storage unit 170. That is, the storage unit 170 may store environment information obtained by the environment information detecting unit 184 and the position information corresponding thereto, and the position information may be an absolute position recognized by the robot cleaner 100 in the cleaning area, or may be a unit cleaning area indicating a region divided on the basis of an obstacle in the cleaning area. Thus, as illustrated in FIG. 8B, using the position information, the control unit 110 may output a temperature distribution regarding at least a portion of the cleaning area on the cleaning map to the screen through the output unit 150, or may transmit the temperature information and the position information to the terminal device 200 so that the terminal device 200 may output the temperature distribution on the cleaning map to the screen. In detail, temperature information indicating that a temperature of the area R1 is "23° C.", a temperature of a portion of the area R2 is "18° C." and a temperature of another portion of the area R2 is "25° C.", a temperature of the area R3 is "15° C.", and a temperature of the area R6 is "27° C." may be output on the cleaning map. Here, the control unit 110 may output the positions or the areas corresponding to the measured temperature information such that they are different in color or shade according to a temperature range to which the measured temperature information belongs among a plurality of preset temperature ranges. Also, the preset temperature ranges may be set to be different according to positions of the cleaning areas, and may be customized according to a user input.

The humidity detecting unit 1842 may include a humidity sensor installed in a predetermined position of the main body of the robot cleaner 100 and measuring ambient humidity. Here, the humidity sensor may measure humidity of at least a portion of a cleaning area and types of the humidity sensor are not particularly limited. Thus, the humidity detecting unit 1842 may measure humidity of at least one portion of the cleaning area and transmit the measured signal to the control unit 110.

The control unit 110 may detect humidity of at least a portion of the cleaning area through the humidity detecting unit 1842. Also, the control unit 110 may store the detected humidity of the at least portion of the cleaning area and a position from which the humidity information was collected, together, in the storage unit 170. That is, the storage unit 170 may store the environment information and position information corresponding thereto obtained by the environment information detecting unit 184, and the position information may be an absolute position recognized by the robot cleaner 100 in the cleaning area, or may be a unit cleaning area indicating an area divided on the basis of an obstacle in the cleaning area. Thus, as illustrated in FIG. 8C, the control unit 110 may output a humidity distribution regarding at least a portion of the cleaning area on the cleaning map to the screen through the output unit 150, or may transmit the humidity information and the position information to the terminal device 200 so that the terminal device 200 may output the humidity distribution on the cleaning map to the screen. In detail, humidity information indicating that humidity of a portion of the area R1 is "55%", humidity of another portion of the area R1 is "57%" or 62%", humidity of a portion of the area R2 is "65%", humidities of other portions of the area R2 are "55%", "50%", or "40%", humidity of the area R3 is "65%" and humidity of another portion of the area R3 is "50%" may be output on the cleaning map. Here, the control unit 110 may output the position or the area corresponding to the measured humidity information on the screen such that a color or shade of the position or the area is different according to a humidity range to which the measured humidity information belongs among a plurality of preset humidity ranges. Also, the preset humidity range may be set to be different according to positions of the cleaning area, and may be customized according to a user input.

The atmospheric pressure detecting unit 1843 may include an atmospheric pressure sensor installed at a predetermined position of the main body of the robot cleaner 100 and measuring ambient atmospheric pressure. Here, any atmospheric pressure sensor may be used as long as it can measure atmospheric pressure of at least a portion of the cleaning area, and types of the atmospheric pressure sensor are not particularly limited. Thus, the atmospheric pressure detecting unit 1843 may measure atmospheric pressure of at least a portion of the cleaning area and transmit a measured signal to the control unit 110.

The control unit 110 may detect the atmospheric pressure of the at least one portion of the cleaning area through the atmospheric pressure detecting unit 1843. Also, the control unit 110 may store the detected atmospheric pressure of the at least portion of the cleaning area and a position from which the atmospheric pressure information has been collected, together, in the storage unit 170. That is, the storage unit 170 may store the environment information obtained by the environment information detecting unit 184 and the position information corresponding thereto, and the position information may be an absolute position recognized by the robot cleaner 100 in the cleaning area or may be a unit cleaning area indicated by a region divided on the basis of an obstacle in the cleaning area. Thus, using the obtained information, the control unit 110 may output an atmospheric pressure distribution of at least a portion of the cleaning area on the cleaning map to the screen through the output unit 150 or may transmit the atmospheric pressure information and the position information to the terminal device 200 so that the terminal device 200 may output the atmospheric pressure distribution on the cleaning map to the screen.

The pollution level detecting unit 1844 may be an air sensor sensing dust or a specific material in the air regarding at least a portion of the cleaning area. In order to sense a specific material contained in the air, the pollution level detecting unit 1844 may suck or diffuse air.

The pollution level detecting unit 1844 may include a gas sensor sensing a material of a specific component such as a $CO_2$ sensor sensing carbon dioxide or an S sensor sensing a sulfur component. Also, the pollution level detecting unit 1844 may include a dust sensor sensing fine dust, a particulate matter, pollen, mite, virus, and the like.

Also, the pollution level detecting unit 1844 may detect yellow dust containing heavy metal such as iron, aluminum, cadmium, lead, and the like, and detect a concentration thereof. Also, the pollution level detecting unit 1844 may detect various colorless and odorless pollutants, for example, radioactive elements such as iodine, cesium, plutonium, and the like, or a harmful gas such as carbon monoxide, ammonia, formaldehyde, a volatile organic compound, and the like.

The control unit 110 may detect a pollution level of air (for example, a concentration of dust or a specific material included in the air, etc.) through the pollution level detecting unit 1844 regarding at least a portion of the cleaning area. Also, the control unit 110 may store the detected air pollution level of the at least one portion of the cleaning area and a position from which the air pollution level information was collected, together, in the storage unit 170. That is, the storage unit 170 may store the environment information obtained by the environment information detecting unit 184 and the position information corresponding thereto, and the position information may be an absolute position recognized by the robot cleaner 100 in the cleaning area or may be a unit cleaning area indicated by a region divided on the basis of an obstacle in the cleaning area. Thus, as illustrated in FIG. 8D, using the obtained information, the control unit 110 may output an air pollution level distribution of at least a portion of the cleaning area on the cleaning map to the screen through the output unit 150 or may transmit the air pollution level information and the position information to the terminal device 200 so that the terminal device 200 may output the air pollution level distribution on the cleaning map on the screen. In detail, information indicating that an air floating particle material has been sensed in a portion of the area R1, a level of $CO_2$ has been increased in a portion of the area R2, a concentration of $O_2$ in a portion of the area R3 is normal, and a gas has been sensed in a portion of the area R6 may be output on the cleaning map. Here, the control unit 110 may output the position or area to be different in color or shade on the screen according to types or levels of pollution level.

At least two of the temperature detecting unit 1841, the humidity detecting unit 1842, the atmospheric pressure detecting unit 1843, and the pollution level detecting unit 1844 described above may be implemented as a single sensor module.

As described above, the control unit 110 is a unit for performing a general function of the robot cleaner 100 using the components included in the robot cleaner 100. Thus, the control unit 110 may perform a function such as traveling in the cleaning area, cleaning the cleaning area, making a cleaning map regarding the cleaning area, and the like, by executing various driving programs or a control program stored in the storage unit 170.

According to a specific embodiment, on the basis of environment information obtained through the environment information detecting unit 184, the control unit 110 may generate a control command regarding the different device 300 in order to adjust environment information regarding at least a portion of a cleaning area, and transmit the generated control command to the different device 300 through the first communication unit 161.

For example, as illustrated in FIG. 10A, in a case in which the robot cleaner 100 is positioned in the area R2 and temperature information among environment information obtained regarding at least a portion of the area R2 is "30°

C.", the control unit 110 may determine that the environment information obtained by the environment information detecting unit 184 is outside of a preset range. Thus, in order to adjust the environment information, the control unit 110 may generate an air conditioning control command regarding a different device (for example, the air conditioner 300b) positioned in the area R2 and transmit the control command generated regarding the different device to the different device through the first communication unit 161, so that the different device may perform an air conditioning operation on the area R2.

Thus, the storage unit 1 70 may store the type of the different device, the position of the different device, the control command regarding the different device, and the like, and also, the storage unit 170 may store the different device corresponding to the type of the environment information, and the like.

Meanwhile, when the control unit 110 generates a control command regarding the different device on the basis of the environment information detected by the environment information detecting unit 184, the control unit 110 may determine whether the detected environment information is outside of a preset range, and here, the preset range may be set to be different according to hours, dates, weeks, months, positions, and seasons. Also, the preset range may be customized according to a user input.

Thus, the robot cleaner according to an embodiment of the present disclosure may provide an optimal environment to the user by adjusting environment information regarding a cleaning area through the robot cleaner and/or a different device such as a home appliance regarding the cleaning area by using information obtained through various sensors provided in the main body of the robot cleaner and a cleaning map generated regarding the cleaning area.

Meanwhile according to another embodiment, in order to adjust environment information regarding at least a portion of the cleaning area on the basis of the environment information obtained through the environment information detecting unit 184, the control unit 110 may transmit the environment information to the terminal device 200 through the second communication unit 162. Thus, upon receiving the environment information, the terminal device 200 may receive a control command from the user and transmit the received control command to the robot cleaner 100 and/or the different device, so that the different device may adjust the environment information according to the control command.

FIG. 9B is a conceptual view illustrating a state in which a robot cleaner, a terminal device, and an SNS server are connected via a network according to an embodiment of the present disclosure. As illustrated in FIG. 9B, the robot cleaner 100 and the terminal device 200 may use the SNS server S to transmit and receive data therebetween, and accordingly, when the environment information is outside of a preset range, the robot cleaner 100 may transmit the environment information in the form of a message to the terminal device 200, or the terminal device 200 may receive a message corresponding to the environment information from the user and transfer the received message to the robot cleaner 100 through the SNS server S.

Thus, the robot cleaner 100 may recognize the received message through the SNS server S, and generate a control command regarding the robot cleaner 100 and/or a different device on the basis of the recognized message.

For example, in a case in which the terminal device is a mobile terminal, as illustrated in FIG. 10B, the robot cleaner 100 and the terminal device 200 (for example, a mobile terminal) may transmit and receive data therebetween through the SNS server S.

In detail, as illustrated in FIG. 10A, in a case in which the robot cleaner 100 is positioned in the area R2 and temperature information among environment information obtained regarding at least a portion of the area R2 is "30° C.", the control unit 110 may determine that the environment information obtained by the environment information detecting unit 184 is outside of a preset range (for example, 18° C. to 24° C.). Thus, the control unit 110 may transmit a message of "Temperature is now increasing. Current indoor temperature is 30° C. Want to operate air conditioner? Or open window?" to the terminal device 200 through the SNS server S by using the second communication unit 162. Thereafter, when a message of "Open the door" is received in response, the terminal device 200 may transfer the received message to the robot cleaner 100 through the SNS server S. The robot cleaner 100 recognizes the received message, and when the received message is a control message corresponding to a different device corresponding to the environment information, the robot cleaner 100 may generate a control command according to the control message. Accordingly, the control unit 110 may transmit the generated control command to a corresponding window control device, a different device corresponding to the control command, to control the window control device to open a window of the area R2.

Thereafter, the robot cleaner 100 may transmit a control command to a different device, and transmit a corresponding control result in the form of a message to the different device through the SNS server S. Also, when the environment information, which was determined to be outside of the preset range, is currently within the preset range after the control command is generated, the control unit 110 may generate a control command different from the previously generated control command, and transmit the generated control command to the corresponding different device. For example, as illustrated in FIG. 10B, after the robot cleaner 100 may receive the control message from the terminal device 200 and generate the corresponding control command, the robot cleaner 100 may transmit a message of "Window is now open. Will close the window when indoor temperature of living room is 24° C." to the terminal device 200.

In this manner, according to an embodiment of the present disclosure, environment information regarding a cleaning area may be adjusted through the robot cleaner and/or a different device such as a home appliance, and here, the robot cleaner 100 may receive a control command in the form of a message from the terminal device 200.

Meanwhile, according to another embodiment, in order to adjust environment information regarding at least a portion of the cleaning area on the basis of the environment information obtained through the environment information detecting unit 184, the storage unit 170 may store the environment information during a predetermined period of time, and the control unit 110 may calculate a predetermined pattern regarding a time range during which the environment information is outside of a preset range, generate a control command regarding the different device before a time range predicted on the basis of the predetermined pattern is reached, and transmit the generated control command to the corresponding different device.

For example, the control unit 110 may predict that at least a portion of the cleaning area is outside of the preset range within a specific time range according to seasons. In detail, on the basis of environment information regarding at least a portion of the cleaning area stored in the storage unit 170, the control unit 110 may calculate a pattern in which the area R2 has a temperature of 30° C. from 1:00 p.m. to 4:00 p.m. in June, July, and August, and may transmit an air conditioning control command to the air conditioner 300b positioned in the area R2 through the first communication unit 161 before 1:00 p.m. in June, July, and August on the basis of the pattern.

In this manner, the robot cleaner according to an embodiment of the present disclosure may adjust environment information regarding the cleaning area through a different device in advance before the environment information moves out of the preset range, thereby providing an optimal environment regarding the cleaning area to the user.

Second Embodiment

The robot cleaner according to the present embodiment includes the details of the first embodiment described above.

Meanwhile, the robot cleaner according to an embodiment of the present disclosure may further include an air purifying unit (not shown).

The air purifying unit (not shown) may be positioned within or outside of the main body of the robot cleaner and may purify air in a contact manner or in a contactless manner. Here, the suction motor 197 may apply a suction force to ambient air to collect ambient air of the robot cleaner. Thus, the air purifying unit (not shown) may be positioned near a hole through which ambient air is sucked to the interior of the cleaner by a suction force of the suction motor 197 or an air flow channel formed to extend from the hole to the suction motor to deodorize or sterilize the sucked air. Accordingly, the control unit 110 may suck ambient air by driving the suction motor 197 and remove a contaminant of the sucked air or deodorize the sucked air.

Here, according to an embodiment of the present disclosure, the air purifying unit may include an ultraviolet (UV) sterilization lamp emitting UV ray of 100 nm to 280 nm to sterilize air or generate ozone and/or a deodorization member deodorizing sucked air or applying scent to the sucked air. In the present disclosure, the method or device for sterilizing and/or deodorizing air is not particularly limited.

According to a specific embodiment, the control unit 110 may purify sucked air using the air purifying unit on the basis of the environment information obtained through the environment information detecting unit 184.

For example, as illustrated in FIG. 8D, in a case in which the robot cleaner 100 detects an air floating particle material in at least a portion of the area R1 through the environment information detecting unit 184, the robot cleaner 100 may move to the area R1 and suck air of the area R1 through the suction motor 197 to purify the sucked air through the air purifying unit.

That is, in order to purify air in at least a portion of the cleaning area, the control unit 110 may perform air purification on the entirety of the cleaning area by utilizing the air purifying unit included in the main body of the robot cleaner 100, rather than transmitting an air conditioning control command to the different device (air purifying device 300c) (please refer to FIG. 9C), and may perform air purification by actively sucking ambient air by utilizing the suction motor for sucking ambient air of the robot cleaner.

Third Embodiment

The robot cleaner according to the present embodiment includes the details of the first and second embodiments described above.

Meanwhile, the robot cleaner according to an embodiment of the present disclosure may detect environment information through the environment information detecting unit 184, or alternatively, the robot cleaner may receive environment information detected by a different device 300 through the first communication unit 161.

FIG. 9C is a conceptual view in which home appliances according to an embodiment of the present disclosure form a home appliance network.

As illustrated in FIG. 9C, at least one home appliance 300 may form a network. Accordingly, the robot cleaner 100 may be connected to the network formed by the home appliances 300 as nodes, and the robot cleaner 100 may receive a value measured by a sensor provided in at least one of the home appliances 300.

Thus, in a case in which any one sensor included in the environment information detecting unit 184 has an error or in a case in which environment information cannot be obtained by the environment information detecting unit 184, the robot cleaner 100 may receive environment information measured by the different device 300 through the home appliance network. That is, a sensor network is established in order top exchange a value measured by the sensor included in the home appliance 300 positioned in the cleaning area, and the robot cleaner according to an embodiment of the present disclosure may utilize the sensor network (please refer to FIG. 11).

Here, a node connected to the sensor network may be a sensor itself or include a device (for example, different device such as the air conditioning device 300a, the air purifying device 300c, or the heating device 300b) including a sensor, in addition to the robot cleaner 100. Thus, environment information that the control unit 110 receives from the sensor network, rather than from the environment information detecting unit 184, may include at least one of a temperature sensed by the temperature detecting unit disposed within the cleaning area, humidity sensed by the humidity detecting unit 400b disposed within the cleaning area, atmospheric pressure sensed by the atmospheric pressure detecting unit 400c disposed within the cleaning area, and an air pollution level sensed by the pollution level detecting unit 400d disposed within the cleaning area (please refer to FIG. 11). In other words, at least one of the temperature detecting unit 400a, the humidity detecting unit 400b, the atmospheric pressure detecting unit 400c, and the pollution level detecting unit 400d may be provided in the different device or may a sensor itself.

Thus, the storage unit 170 may store position information of the node connected to the sensor network, specifically, position information regarding the different device 300, the sensor, or the like, within the cleaning area, and the first communication unit 161 may receive environment information from the different device 300 through the network, thus obtaining environment information of the position corresponding to the position information of the different device 300.

According to an embodiment of the present disclosure, the control unit 110 may transmit a control command generated on the basis of environment information obtained from the environment information detecting unit 184 and/or the sensor network to the different device 300 through the first communication unit 161 (please refer to the descriptions of the first embodiment) or may sterilize and/or deodorize sucked air by using the air purifying unit (not shown) (please refer to the descriptions of the second embodiment)

Thus, the robot cleaner according to an embodiment of the present disclosure may not need to include all the sensors corresponding to environment information to obtain the environment information, and even though any one sensor has an error, environment information intended to be obtained from the erroneous sensor may be received from a different device, thus obtaining environment information.

Method of Controlling Robot Cleaner

FIG. 12 is a flow chart illustrating a sequential process of a method of controlling a robot cleaner according to an embodiment of the present disclosure. As illustrated in FIG. 12, a method of controlling a robot cleaner according to an embodiment of the present disclosure may include: step (S10) of obtaining environment information regarding at least a portion of a cleaning area, step (S20) of generating a control command regarding a different device positioned within the cleaning area in order to adjust the environment information on the basis of the environment information, and step (S30) of transmitting the control command to the different device.

Hereinafter, the method of controlling a robot cleaner according to an embodiment of the present disclosure and each component will be described with reference to FIGS. 1 through 11, and descriptions of the same parts will be replaced by the above descriptions and detailed description thereof will be omitted.

In step (S10) of obtaining environment information, at least one environment information among a temperature, humidity, atmospheric pressure, and an air pollution level may be detected through the environment information detecting unit 184, or environment information detected by the home appliance 300 may be received through the first communication unit 161.

In step (S20) of generating a control command regarding a different device, in a case in which environment information detected by the environment information detecting unit 184 or environment information received from the different device 300 is outside of a preset range, a control command for adjusting the environment information may be generated for the different device corresponding to a type of the environment information.

Accordingly, the storage unit 170 may store the type of the different device, the position of the different device, the control command regarding the different device, and also, the storage unit 170 may store information related to the different device corresponding to the type of the environment information.

In step (S30) of transmitting a control command to a different device, the control command generated by the control unit 110 may be transmitted to the different device 300 corresponding to the environment information or the control command through the first communication unit 161.

Meanwhile, as illustrated in FIG. 13, the method of controlling a robot cleaner according to another embodiment of the present disclosure may further include steps (S11 and S12) of transmitting the environment information to a terminal device through an SNS server when the environment information is outside of a preset range, and step (S13) of receiving a control message regarding the different device from the terminal device through the SNS server, and here, in step (S30) of generating the control command, a control command regarding the different device may be generated on the basis of the control message.

In steps (S11 and S12) of transmitting environment information to the terminal device through the SNS server S, the control unit 110 may transmit the environment information to the terminal device 200 in order to adjust the environment information regarding at least a portion of the cleaning area on the basis of the environment information obtained through the environment information detecting unit 184 or obtained from the different device 300 through the first communication unit 161. Here, when the environment information is transmitted to the terminal device 200 through the SNS server S, the environment information may be transmitted in the form of a message.

Thus, upon receiving the environment information, the terminal device receives a control command from the user, and the robot cleaner 100 may receive the control command, which has been received from the user, from the terminal 200 through the SNS server S (S13).

The terminal device 200 receives the environment information in the form of a message from the robot cleaner 100, and thereafter, when the terminal device 200 transmits and receives data in a message format such that a control message is transmitted to the robot cleaner 100, or the like, the terminal device 200 may output the message on a screen in an interactive manner as illustrated in FIG. 10B.

Thus, the robot cleaner 100 may recognize the message received through the SNS server S, generate a control command regarding the robot cleaner 100 and/or a different device on the basis of the recognized message, and transmit the generated control command to the different device 300 corresponding to the environment information or the control command (S30).

Thereafter, the robot cleaner 100 may transmit a control command to the different device and transmit a corresponding control result in a message format to the different device again through the SNS server S (not shown). Also, when the environment information, which was determined to be outside of the preset range, is currently within the preset range after the control command is generated, the control unit 110 may generate a control command different from the previously generated control command, and transmit the generated control command to the corresponding different device.

Meanwhile, according to another embodiment of the present disclosure, as illustrated in FIG. 14, step (S10) of obtaining the environment information, the air sensor may sense dust in the air of a material included in the air, and the method of controlling a robot cleaner may further include steps (S40 and S50) of deodorizing or sterilizing sucked air on the basis of pollution information sensed by the air sensor.

In step (S10) of obtaining environment information, an air pollution level may be sensed through the environment information detecting unit 184 or an air pollution level sensed by the home appliance 300 (for example, the air conditioning device or the air purifying device) may be received through the first communication unit 161.

In step (S40) of sucking air, the suction motor 197 may be driven to allow ambient air to be sucked into the robot cleaner 100 by suction force of the suction motor 197.

Thereafter, the air purifying unit (not shown) positioned in an air flow channel formed within the cleaner by suction force of the suction motor 197 may deodorize or sterilize sucked air.

That is, unlike the previous embodiment, in order to purify air in at least a portion of the cleaning area, the control unit 110 may perform air purification on the entirety of the cleaning area by utilizing the air purifying unit included in the main body of the robot cleaner 100, rather than transmitting an air conditioning control command to the different device (air purifying device 300c) (please refer to FIG. 9C), and may perform air purification by actively sucking ambient air by utilizing the suction motor for sucking ambient air of the robot cleaner.

The method of controlling a robot cleaner according to an embodiment of the present disclosure described above may be implemented in the form of a program command that may be performed through various computer components and recorded in a computer-readable recording medium.

The invention claimed is:

1. A robot cleaner comprising:
an environment information detecting unit configured to obtain environment information regarding at least a portion of a cleaning area;
a first communication unit configured to transmit and receive data to and from a different device positioned within the cleaning area;
a control unit configured to generate a control command regarding the different device in order to adjust the obtained first environment information; and
a second communication unit configured to transmit and receive data to and from a terminal device,
wherein the control unit is configured to:
receive, at the first communication unit, second environmental information from the different device;
determine whether the second environmental information, received at the first communication unit, is outside the preset range;
when the second environmental information is determined to be outside the preset range, control the second communication unit to transmit the second environmental information to the terminal device through an SNS server;
receive, at the second communication unit and through the SNS server, a control message regarding the different device;
provide, based on the received control signal, a control command regarding the different device; and
control the first communication unit to transmit, to the different device, the control command regarding the different device,
an obstacle detecting unit configured to detect an obstacle of the cleaning area using at least one sensor; and
a position recognizing unit configured to recognize a position of the robot cleaner using at least one sensor,
wherein the control unit generates a cleaning map regarding the cleaning area on the basis of information regarding the obstacle detected by the obstacle detecting unit and information regarding the position recognized by the position recognizing unit,
wherein the environment information detecting unit comprises an air sensor configured to sense dust in the air or a material included in the air,
an air purifying unit configured to deodorize or sterilize sucked air,
wherein the control unit purifies the sucked air using the air purifying unit on the basis of pollution information sensed by the air sensor;
a storage unit configured to store position information regarding the different device,
wherein the control unit recognizes environment information of a position corresponding to the position information of the different device, as environment information detected by the different device.

2. The robot cleaner of claim 1 wherein the storage unit is configured to store the second environment information and corresponding position information.

3. The robot cleaner of claim 1, wherein the control unit generates a control command regarding a different device at a position corresponding to the second environment information.

4. The robot cleaner of claim 1, wherein the environment information detecting unit detects at least one of a temperature, humidity, atmospheric pressure, and an air pollution level around the robot cleaner.

5. The robot cleaner of claim 1 wherein the storage unit is configured to store environment information for a predetermined period of time, wherein the control unit calculates a predetermined pattern regarding a time range in which the first environment information is outside of a preset range, and generates a control command regarding the different device before the time range estimated on the basis of the predetermined pattern is reached.

6. The robot cleaner of claim 1, wherein the storage unit is configured to store the first environment information and corresponding position information, wherein the position information is information indicating a region divided on the basis of the obstacle in the cleaning area.

7. The robot cleaner of claim 1, wherein the second environment information includes at least one of a temperature, humidity, atmospheric pressure, and an air pollution level.

8. The robot cleaner of claim 1, further comprising:
an output unit configured to output the second environment information to the outside in a visual or audible manner.

9. The robot cleaner of claim 8, wherein, when the second environment information is outside of a preset range, the control unit outputs an alarm signal through the output unit.

10. A remote control system of a robot cleaner, the remote control system comprising:
the robot cleaner according to claim 1; and
the terminal device configured to generate a control command regarding the robot cleaner and the different device.

* * * * *